United States Patent [19]

Shyjan

[11] Patent Number: 5,994,130
[45] Date of Patent: Nov. 30, 1999

[54] MULTIDRUG RESISTANCE-ASSOCIATED POLYPEPTIDE

[75] Inventor: Andrew Shyjan, Nahant, Mass.

[73] Assignee: Millennium Pharmaceuticals, Inc., Cambridge, Mass.

[21] Appl. No.: 09/001,273

[22] Filed: Dec. 31, 1997

Related U.S. Application Data

[62] Division of application No. 08/843,459, Apr. 16, 1997.

[51] Int. Cl.[6] .......................... C12N 15/10; C12N 15/63; C12N 15/12
[52] U.S. Cl. .................. 435/325; 435/252.3; 435/320.1; 435/69.1; 435/366; 435/254.2; 536/23.5; 536/23.1
[58] Field of Search ................................ 435/325, 352.3, 435/320.1, 69.1, 366, 254.2; 536/23.5, 23.1

[56] References Cited

U.S. PATENT DOCUMENTS

| | | | |
|---|---|---|---|
| 5,104,858 | 4/1992 | Hait et al. | 514/34 |
| 5,182,293 | 1/1993 | Sunkara et al. | 514/340 |
| 5,190,946 | 3/1993 | Ramu et al. | 514/255 |
| 5,190,957 | 3/1993 | Sunkara et al. | 514/314 |
| 5,262,311 | 11/1993 | Pardee et al. | 435/91.2 |
| 5,369,009 | 11/1994 | Arceci et al. | 435/7.23 |
| 5,387,685 | 2/1995 | Powell et al. | 546/143 |
| 5,403,574 | 4/1995 | Piwnica-Worms | 424/1.65 |
| 5,407,653 | 4/1995 | Piwnica-Worms | 424/1.11 |
| 5,489,519 | 2/1996 | Deeley et al. | 435/69.1 |
| 5,510,239 | 4/1996 | Baracchini, Jr. et al. | 435/6 |
| 5,523,304 | 6/1996 | Sunkara | 514/277 |
| 5,543,423 | 8/1996 | Zelle et al. | 514/332 |
| 5,550,149 | 8/1996 | Powell et al. | 514/416 |
| 5,556,856 | 9/1996 | Engel et al. | 514/248 |
| 5,561,141 | 10/1996 | Powell et al. | 514/311 |
| 5,599,672 | 2/1997 | Liang et al. | 435/6 |

FOREIGN PATENT DOCUMENTS

| | | |
|---|---|---|
| WO 94/10303 | 5/1994 | WIPO . |
| WO 95/10938 | 4/1995 | WIPO . |
| WO95/27784 | 10/1995 | WIPO . |
| WO95/31474 | 11/1995 | WIPO . |
| WO96/02556 | 2/1996 | WIPO . |
| WO96/06945 | 3/1996 | WIPO . |
| WO 97/31111 | 8/1997 | WIPO . |

OTHER PUBLICATIONS

Hamilton et al. (1984), "Experimental Model Systems of Ovarian Cancer: Applications to the Design and Evaluation of New Treatment Approaches," 11 *Semin. Oncol.* 3:285–298.

Batist et al. (1986), "Overexpression of a Novel Anionic Gluthathione Transferase in Multidrug–Resistant Human Breast Cancer Cells," 261 *J. Biol. Chem.* 33:15544–15549.

Marsh et al. (1986), "Isolation and Characterization of Adriamycin–resistant HL–60 Cells Which Are Not Defective In The Initial Intracellular Accumulation of the Drug," 46 *Cancer Res.* 4053–4057.

Mirski et al. (1987), "Multidrug Resistance in a Human Small Cell Lung Cancer Cell Line Selected in Adriamycin," 47 *Cancer Res.* 2594–2598.

Hyde et al. (1990), "Structural Model of ATP–binding Proteins Associated With Cystic Fibrosis, Multidrug Resistance and Bacterial Transport," 346 *Nature* 362–365.

Krishan (1990), "Rapid Determination of Cellular Resistance–Related Drug Efflux in Tumor Cells," 33 *Meth. Cell Biol.* 491–500.

Cole et al. (1992), "Overexpression of a Transporter Gene in a Multidrug–Resistant Human Lung Cancer Cell Line," 258 *Science* 1650–1654.

Higgins (1992), "ABC Transporters: From Microorganisms to Man," 8 *Annu. Rev. Cell Biol.* 67–113.

Cole (1993), "Multidrug Resistance–Associated Protein: Sequence Correction," 260 *Science* 879.

Egholm et al. (1993), "PNA Hybridizes to Complementary Oligonucleotides Obeying the Watson–Crick Hydrogen–Bonding Rules," 365 *Nature* 566–568.

Zaman et al. (1993), "Analysis of the Expression of MRP, the Gene For A New Putative Transmembrane Drug Transporter, in Human Multidrug Resistant Lung Cancer Cell Lines," 53 *Cancer Res.* 1747–1750.

Cole et al. (1994), "Pharmacological Characterization of Multidrug Resistant MRP–Transfected Human Tumor Cells," 54 *Cancer Res.* 5902–5910.

Ravnik–Glavac et al. (1994), "Sensitivity of Single–Strand Conformation Polymorphism and Heteroduplex Method For Mutation Detection in The Cystic Fibrosis Gene," 3 *Human Mol. Gen.* 5:801–.

Slapak et al. (1994), "Expression of the Multidrug Resistance Associated Protein and P–Glycoprotein in Doxorubicin–Selected Human Myeloid Leukemia Cells," 84 *Blood* 9:3113–3121.

(List continued on next page.)

*Primary Examiner*—Rebecca E. Prouty
*Assistant Examiner*—Richard Hutson
*Attorney, Agent, or Firm*—Lahive & Cockfield, LLP

[57] ABSTRACT

Compositions and methods are disclosed for improving the effectiveness of a chemotherapeutic regimen to eradicate multidrug-resistant transformed cells from the body of a mammal, preferably from the body of a human. The present disclosure capitalizes on the discovery of a novel multidrug-resistance associated protein (MRP), herein designated MRP-β. The disclosed compositions include MRP-α nucleic acids, including probes and antisense oligonucleotides, MRP-β polypeptides and antibodies, MRP-β expressing host cells, and non-human mammals transgenic or nullizygous for MRP-β. The disclosed methods include methods for attenuating aberrant MRP-β gene expression, protein production and/or protein function. In addition, methods are disclosed for identifying and using a modulator, such as an inhibitor, of MRP-β. Preferably, the modulator is a small molecule.

10 Claims, 9 Drawing Sheets

OTHER PUBLICATIONS

Zaman et al. (1994), "The Human Multidrug Resistance Associated Protein MRP is a Plasma Membrane Drug–Efflux Pump," 91 *Proc. Nat'l. Acad. Sci. USA* 8822–8826.

Almquist et al. (1995), "Characterization of the $M_r$ 190,000 Multidrug Resistance Proteins (MRP) in Drug–Selected and Transfected Humor Tumor Cells," 55 *Cancer Res.* 120–110.

Lautier et al. (1996), "Multidrug Resistance Mediated by the Multidrug Resistance Protein (MRP) Gene," 52 *Biochem. Pharmacol.* 967–977.

Perry–O'Keefe et al. (1996), "Peptide Nucleic Acid Pre–Gel Hybridization: An Alternative to Southern Hybridization," 93 *Proc. Natl. Acad. Sci. USA* 14670–14675.

Ruetz et al. (1996), "Functional Expression of the Multidrug Resistance–Associated Protein in the Yeast *Saccharomyces cerevisiae*," 271 *J. Biol. Chem.* 8:4154–4160.

Stewart et al. (1996), "Reduction of Expression of the Multidrug Resistance Protein (MRP) in Human Tumor Cells by Antisense Phosphorothioate Oligonucleotides," 51 *Biochem. Pharmacol.* 461–469.

Stride et al. (1996), "Structure and Expression of the Messenger RNA Encoding the Murine Multidrug Resistance Protein, and ATP–Binding Cassette Transporter," 49 *Mol. Pharmacol.* 962–971.

Sager (1997), "Expression Genetics in Cancer: Shifting the Focus From DNA to RNA," 94 *Genetics* 952–955.

Mark D. Adams et al., Nature 377 (Supp):3–17, Sep. 28, 1995.

Rando Allikmets et al., Hum. Mol. Genet. 5 (10):1649–1655, Mar. 26, 1997.

L. Hillier et al., WashU–Merck EST Project, Genbank Accession No. H17207, Jun. 29, 1995.

Suzuki, T., et al., "cDNA cloning of a short type of multidrug resistance protein homologue, SMRP, from a human lung cancer cell line" *Biochemical and Biophysical Research Communications* 238(3):790–4 (1997).

Kool, M., et al., "Four homologs of the multidrug resistance protein MRP1" *Eighty–Eighth Annual Meeting of the American Association for Cancer Research,* San Diego, CA, Apr. 12–15, 1997, Proceedings of the American Association for Cancer Research Annual Meeting, 38(0), (1997), abstract#2941.

Genbank® Accession No. H17207 for ym42a06.rl Soares infant brain 1NIB Homo sapiens cDNA clone 50857 5' similar to SP:MRP_Human P33527 Multidrug Resistance-Associated; mRNA sequence.

FIGURE 1A

| | | | | | | | | | | | | | | | | | | | | AA# | nt# |
|---|---|---|---|---|---|---|---|---|---|---|---|---|---|---|---|---|---|---|---|---|---|
| | D | V | K | L | T | V | C | E | P | W | N | L | H | S | E | K | M | K | D | 19 | 58 |
| T | GAT | GTG | AAA | CTA | ACA | GTC | TGT | GAG | CCC | TGG | AAC | CTC | CAC | TCA | GAG | AAG | ATG | AAG | GAT | | |
| I | D | I | G | K | E | Y | I | P | S | P | G | Y | R | S | V | R | E | R | | 39 | 118 |
| ATC | GAC | ATA | GGA | AAA | GAG | TAT | ATC | CCC | AGT | CCT | GGG | TAT | AGA | AGT | GTG | AGG | GAG | AGA | | | |
| T | S | T | . | T | H | R | D | R | D | S | K | F | R | T | R | P | | | | 59 | 178 |
| ACC | AGC | ACT | TCT | GGG | ACG | CAC | AGA | GAC | CGT | GAT | TCC | AAG | TTC | AGG | AGA | ACT | CGA | CCG | | | |
| L | E | C | Q | D | A | L | E | T | A | R | A | E | G | L | S | L | D | A | | 79 | 238 |
| TTG | GAA | TGC | CAA | GAT | GCC | TTG | GAA | ACA | GCA | CGA | GCC | GAG | GGC | CTC | TCT | CTT | GAT | GCC | | | |
| S | M | H | S | Q | L | R | I | L | D | E | H | P | K | G | Y | H | H | | | 99 | 298 |
| TCC | ATG | CAT | TCT | CAG | CTC | AGA | ATC | CTG | GAT | GAG | GAG | CAT | CCC | AAG | TAC | CAT | CAT | | | | |
| G | L | S | A | L | K | P | I | R | T | S | W | H | Q | L | A | R | V | A | H | 119 | 358 |
| GGC | TTG | AGT | GCT | CTG | AAG | CCC | ATC | CGG | ACT | TCG | TGG | CAC | CAG | CTG | GCC | CGT | GTG | GCC | CAC | | |
| A | G | L | F | S | C | M | T | M | E | D | V | W | S | K | H | E | S | D | | 139 | 418 |
| GCT | GGG | CTT | TTT | TCC | TGT | ATG | ACT | ATG | GAA | GAC | GTG | TGG | TCA | AAG | CAC | GAG | TCT | GAC | | | |
| K | K | G | E | L | S | R | R | L | E | R | L | W | Q | E | E | N | E | V | S | 159 | 478 |
| AAG | AAG | GGG | GAG | CTC | TCA | AGA | AGA | CTA | GAG | AGA | CTG | TGG | CAA | GAA | GAG | AAT | GAA | GTT | TCT | | |
| V | N | C | R | L | M | I | T | R | V | W | I | A | G | F | S | F | C | R | T | G | 179 | 538 |
| GTG | AAC | TGC | AGA | AGA | CTG | ATG | ATC | ACG | AGG | GTT | TGG | ATC | GCT | GGC | TTC | TTC | TGC | CGC | ACC | GGG | |
| L | S | P | D | 199 | 598 |
| A | A | S | L | R | L | M | R | R | V | V | L | A | G | E | S | G | P | | | |
| GCT | GCT | TCC | CTC | CGA | CTA | ATG | AGG | AGG | GTG | GTT | CTG | GCT | GGA | GAG | AGT | GGA | CCA | | | | |
| V | C | L | M | I | T | Q | W | A | F | S | A | M | V | L | V | S | K | H | 219 | 658 |
| GTG | TGC | CTG | ATG | ATC | ACG | CAG | TGG | GCT | TTC | AGT | GCT | ATG | GTG | CTG | GTG | TCC | AAA | CAC | | | |
| L | L | E | Y | T | Q | A | T | E | S | N | L | Q | Y | L | V | L | L | 239 | 718 |
| CTC | TTG | GAG | TAT | ACC | CAG | GCA | ACA | CAG | TCT | AAC | CTG | CAG | TAC | AGC | TTG | TTA | GTG | CTG | | | |

FIGURE 1A

```
  G   L   L   T   E   I   V   R   S   W   L   A   L   T   W   A   L   N
  GGC CTC CTG ACG GAA ATC GTG CGG TCT TGG CTT GCA CTG ACT TGG GCA TTG AAT    259
                                                                              778

Y   R   T   V   R   L   R   G   A   I   L   T   M   A   F   L   I   L
  TAC CGA ACC GTC CGC TTG CGG GGG GCC ATC CTA ACC ATG GCA TTT CTA ATC CTT    279
                                                                              838

K   L   N   I   K   E   A   K   S   L   E   N   I   C   G   S   N   D
  AAG TTA AAC ATT AAA GAG GCA AAA TCC CTG GAG AAC ATT TGC GGT TCC AAC GAT    299
                                                                              898

G   Q   R   M   F   E   A   Y   V   G   S   L   A   L   G   G   P   V
  GGG CAG AGA ATG TTT GAG GCA TAT GTA GGC AGC CTG GCT CTG GGA GGA CCC GTT    319
                                                                              958

A   I   L   G   M   I   F   L   Y   P   A   T   L   G   F   T   A   S
  GCC ATC TTA GGC ATG ATT TTT CTC TAC CCA GCA ACA CTG GGA TTC ACA GCA TCA    339
                                                                             1018

A   V   F   L   V   M   R   E   D   A   T   S   R   K   M   N   Y   F
  GCT GTT TTT CTC GTG ATG CGT GAA GAT GCC ACG TCA CGG AAG ATG AAT TAC TTC    359
                                                                             1078

R   R   K   A   W   E   K   A   S   F   Y   T   V   Q   S   Q   L   T
  AGG AGA AAA GCA TGG GAA AAA GCC AGC TTT TAC ACC GTG CAG AGT CAG CTT ACT    379
                                                                             1138

Y   I   K   E   R   R   I   V   L   E   A   G   V   V   S   I   Q   K
  TAC ATT AAA GAG GAG CGT CGG ATA TTG GAA GCC GGG GTC GTT AGC ATC CAG AAA    399
                                                                             1198

I   R   E   E   I   V   V   A   Q   A   A   F   T   V   H   I   T   V
  ATC CGC GAG GAG ATT GTG GTG GCA CAG GCA GCA TTC ACC GTG CAT ATC ACT GTG    419
                                                                             1258

G   V   A   P   I   V   A   A   T   L   T   T   V   V   S   F   V   E   M
  GGT GTG GCT CCC ATT GTG GCA GCA ACG CTG ACA ACC GTG GTG TCT TTC GTC GAA ATG  439
                                                                               1318

L   G   F   D   L   T   L   T   A   A   V   V   L   S   F   N   S   M
  CTG GGC TTC GAT CTG ACA CTG ACA GCA GCA GTG GTG CTC TCA TTC AAT TCC ATG    459
                                                                             1378

T   F   A   L   K   V   T   P   F   S   V   K   V   A   S   V   A
  ACT TTT GCT TTG AAA GTA ACA CCG TTT TCA GTA AAG GTC GCC TCA GTG GCT        479
                                                                             1438
```

```
     V   D   R   F   K   S   L   L   M   E   E   V   H   M   I   K   N   K   P       499
    GTT GAC AGA TTT AAG AGT TTG CTA ATG GAA GAG GTT CAC ATG ATA AAG AAC AAA CCA      1498

A   S   P   H   I   Q   N   F   E   M   K   T   N   A   L   A   W   D   S   H  519
    GCC AGT CCT CAC ATC CAG AAC TTT GAG ATG AAA ACC AAT GCC TTG GCA TGG GAC TCC CAC 1558

S   S   I   Q   N   L   P   T   K   M   P   K   K   D   R   V   R   A   S       539
    TCC AGT ATC CAG AAC CTG CCC ACC AAA ATG CCC AAA AAG GAC AGG GTG AGG GCT TCC      1618

R   G   K   K   E   K   R   R   Q   D   R   E   P   K   A   E   E   R   A       559
    AGG GGC AAG AAA GAG AAG AGG CGC CAG GAC CGG GAG CCC AAG GCG GAG GAG AGG GCA      1678

E   Q   K   H   L   D   S   R   E   L   C   Q   P   T   V   G   S   E   E       579
    GAG CAG AAA CAC CTG GAC AGT CGC GAG TTA TGC CAG CCC ACA GTG GGC AGT GAA GAA      1738

G   I   H   L   H   V   G   L   G   K   L   G   S   H   I   A   L   N   D       599
    GGC ATC CAC CTC CAC GTT GGC CTG GGA AAA CTG GGA AGC CAC ATT GCA CTG AGT GAT      1798

E   Q   A   L   M   T   W   A   Q   Q   E   N   L   I   S   G   R   T   S       619
    GAG CAA GAG CTG ATG ACG TGG GCC CAG CAG GAG AAT CTA ATC AGT GGA AGA ACC TCT      1858

L   I   S   A   V   E   Y   R   E   A   E   Y   N   S   F   T   L   S   G       639
    CTC ATT TCA GCC GTG GAG GAA AGA AAT TCT TAC ACT TTC ACG AGC AGT AGT GAT GGA      1918

T   F   A   Y   E   K   D   Q   E   S   D   L   T   E   I   G   E   D   N   I  659
    ACC TTC GCT TAT GTG GAG AAG GAT CAG GAA TCC AGC GAC CTG ACG GAG ATT GAG GAC ATC 1978

L   F   G   E   A   I   L   P   Y   N   S   L   T   F   C   L   C             679
    CTG TTT GGG GAA GCC TAT ATT CTT CCC TAC AAC TCT CTG ACG TGC TGC CTG              2038

R   P   D   L   K   Y   S   R   S   I   G   E   I   Y   R   S   G   A           699
    AGG CCT GAC CTG AAG TAT AGC AGC ATC GGA ATT GGA GAG GAG TAT CGA GGA GCC          2098

N   L   S   G   G   Q   R   Q   R   I   S   L   A   R   A   L   Y   S   D   R  719
    AAC CTG AGC GGT GGG CAG CGC CAG ATC AGC CTT GCC CGG GCC CTT TAT AGT GAC AGG     2158
```

| | | | | | | | | | | | | | | | | | | | |
|---|---|---|---|---|---|---|---|---|---|---|---|---|---|---|---|---|---|---|---|
| S | I | Y | I | D | D | P | L | S | A | L | D | A | H | V | G | N | H | I | 739 |
| AGC | ATC | TAC | ATC | GAC | GAC | CCC | CTC | AGT | GCC | TTA | GAT | GCC | CAT | GTG | GGC | AAC | CAC | ATC | 2218 |
| F | N | S | A | I | R | K | H | L | L | K | S | I | V | F | L | T | H | Q | 759 |
| TTC | AAT | AGT | GCT | ATC | CGG | AAA | CAT | CTC | CTC | AAG | TCC | ATC | GTT | TTT | CTG | ACC | CAC | CAG | 2278 |
| L | Q | Y | L | V | D | C | D | E | V | I | F | G | C | I | T | E | 779 |
| TTA | CAG | TAC | CTG | GTT | GAC | TGT | GAT | GAA | GTG | ATC | TTC | GGC | TGT | ATT | ACC | GAA | 2338 |
| R | G | T | H | E | E | L | M | N | L | M | D | Y | A | K | E | G | I | F | N | 799 |
| AGA | GGC | ACC | CAT | GAG | GAA | CTG | ATG | AAT | TTA | ATG | GAC | TAT | GCT | AAA | GAG | GGT | ATT | TTT | AAC | 2398 |
| L | L | G | S | E | T | P | P | K | D | Q | I | S | K | T | G | S | 819 |
| CTG | TTG | GGA | TCA | GAG | ACA | CCG | CCA | AAG | GAC | CAG | ATC | TCA | AAA | ACA | GGA | AGT | 2458 |
| Q | K | P | E | Q | Q | L | A | E | E | K | I | K | E | G | S | V | 839 |
| CAG | AAG | CCA | GAG | CAA | CAG | CTT | GCT | GAG | GAG | AAA | ATA | AAG | GAA | GGG | TCA | GTA | 2518 |
| K | P | V | Y | N | V | G | F | A | T | S | G | L | A | P | W | 859 |
| AAG | CCA | GTA | TAC | AAT | GTA | GGG | TTC | GCT | ACC | AGC | GGT | TTG | GCA | CCC | TGG | 2578 |
| S | V | F | Q | Y | I | N | V | T | T | V | Y | A | L | W | I | 879 |
| TCA | GTA | TTT | CAA | TAC | ATC | AAT | GTA | ACT | ACT | GTG | TAC | GCC | CTC | TGG | ATT | 2638 |
| A | L | Q | N | G | S | T | M | E | W | S | T | N | E | Y | S | W | 899 |
| GCC | CTT | CAA | AAT | GGG | AGC | ACC | ATG | GAG | TGG | AGC | ACC | AAC | GAG | TAC | TCG | TGG | 2698 |
| I | K | M | D | G | H | M | Q | V | Y | A | S | I | V | S | D | 919 |
| ATC | AAG | ATG | GAC | GGG | CAT | ATG | CAG | GTG | TAT | GCC | AGC | ATC | GTG | TCC | GAC | 2758 |
| S | M | K | D | N | P | A | I | R | G | V | F | V | K | M | A | 939 |
| AGC | ATG | AAG | GAC | AAT | CCT | GCC | ATT | CGA | GGA | GTT | TTT | GTC | AAG | ATG | GCA | 2818 |
| V | M | L | K | A | L | I | L | K | T | L | R | A | 959 |
| GTC | ATG | CTG | AAA | GCC | ATT | CTG | AAA | ACG | CTG | CGA | GCT | 2878 |

```
  S   S   R   L   H   D   E   L   F   R   R   I   L   R   S   P   M   K   F   F    979
 TCC TCC CGG CTG CAT GAC GAG CTT TTC CGA AGG ATC CTT CGA AGC CCT ATG AAG TTT TTT   2938

D   T   P   T   G   R   N   R   I   L   S   D   M   E   V                         999
 GAC ACG CCC ACA GGG AGG AAC AGG ATT CTC TCC GAC ATG GAA GTT                        2998

V   R   L   P   Q   F   A   E   M   L   N   F   I   Q   L   V   P   F   L   D    1019
 GTG CGG CTG CCG TTC CAG GCC GAG ATG CTC AAC TTC ATC CAG CTG GTG CCC TTC TTC GAC   3058

V   G   M   I   A   G   V   F   P   W   R   F   L   V   G   P   K   L   V   C    1039
 GTG GGA ATG ATC GCA GGA GTC TTC CCG TGG AGG TTC CTT GTG GGG CCC AAG CTT GTC TGT   3118

L   F   S   V   L   H   P   F   L   Q   V   R   I   L   I   E   L   R   L   I    1059
 CTC TTT TCA GTC CTG CAC CCT TTC CTC CAG GTC CGT ATA CAG GAG CTG CGT CTG ATC       3178
                                CTG

N   I   T   Q   N   P   K   F   F   F   G   Q   L   H   T   A   M   Y   A   D    1079
 AAT ATC ACG CAG AAT CCT AAA GGG CAG TTT TTT TTG CTC ACG CAC GCG ATG TAC GCC GAC   3238

I   H   A   Y   A   P   F   T   C   T   T   L   A   E   V   R   M   T   D   T    1099
 ATC CAC GCC TAC GCC CCT TTT ACG TGT ACA ACC CTG GCG GAG GTT CGG ATG ACG GAC ACC   3298

N   Q   A   P   F   F   L   F   T   I   G   L   L   A   V   W   L   A   D   D    1119
 AAC CAA GCT CCT TTT TTT TTG TTT ACC ATC GGG GGT CTC GCT GCA GTT TGG CTG GCT GAT   3358

L   I   S   A   Y   L   L   S   E   T   E   A   R   F   Q   V   L   R   H   Q    1139
 CTC ATC AGC GCC TAT CTC TCT GCA TCT GAG ACA GAA GCT CGA TTC CAG GTT CTG CAC CAG   3418
                                                                        CGG

I   P   P   A   Y   V   A   R   I   A   P   A   R   F   T   S   V   G   L   F    1159
 ATT CCC CCA GCC TAT GTC GCG ATC GCC CCT GCA CGA TTC ACC TCG GGG CTG TTC             3478

Q   F   T   V   R   L   A   S   E   T   E   A   P   A   R   F   S   V   E   I    1179
 CAG TTT ACG GTC AGA CTG GCA TCT GAG ACA GAA GCA CCT GCC CGA TTC TCC GTG GAG ATC   3538

N   H   Y   I   K   T   L   S   S   L   E   A   R   A   K   N   K   A   P        1199
 AAT CAC TAC ATT AAG ACT CTG TCC TTG GAA GCA AGA GCC AAG AAC AAG GCT CCC            3598
```

```
S   P   D   W   Q   E   G   E   V   T   F   E   N   A   E   M   R   Y   R       1219
TCC CCT GAC TGG CAG GAG GGA GAG GTG ACC TTT GAG AAC GCA GAG ATG AGG TAC CGA      3658

E   N   L   P   Q   V   L   K   G   E   K   V   S   F   T   I   K   E   I       1239
GAA AAC CTC CCT CTC GTC CTA AAG AAA GTA TCC TTC ACG ATC AAA GAG AAG ATT         3718

G   I   V   G   R   T   G   S   K   G   L   S   A   M   I   F   R   L   L       1259
GGC ATT GTG GGG CGG ACA GGA TCA AAG GGG TCG CTG GCC ATG ATC TTC CGT CTG         3778

V   E   L   S   C   G   H   K   I   D   G   V   R   I   S   D   L   G   L       1279
GTG GAG TTA TCT TGC GGC TGC AAG ATT GAT GGA GTG AGT GAT ATT GGC CTT             3838

A   D   L   R   S   L   D   P   K   D   P   Y   Q   P   E   D   F   L   T       1299
GCC GAC CTC CGA AGC CTC TCT GAC CCC AAA GAT CCT CAA CCT GAG GAC TTT ACT         3898

V   R   S   N   L   M   K   E   C   N   F   S   Q   T   Y   A   Q   L   L       1319
GTC AGA TCA AAT TTG ATG AAA GAA TGT AAC TTC TCA CAG ACT TAC ATA CAG CTG         3958

E   R   T   H   G   D   P   K   I   E   T   S   V   L   E   I   A   R   A       1339
GAG ACA CAC GGG GAT CCT AAG ATT GAG ACC TCA GTG TTG GAA ATA GCT AGA GCC         4018

M   E   N   H   C   I   Q   E   F   A   F   R   E   A   D   C   T   M   T   E   1359
ATG GAG AAT CAC TGT ATC CAA GAA TTC GCA TTT CGA GAA GCT GAC TGT GCC ATG ACA GAG 4078

L   L   R   L   T   Q   K   H   Q   T   E   A   F   D   R   I   M   L   T       1379
CTG CTC CGC CTG TTG ATT CAA ACC GAG GAA GCA TTT CGA GAT AGG ATG CTG ACC         4138

T   D   L   H   L   T   I   Q   E   T   V   L   G   S   D   R   L   A   Q   G   1399
ACA GAC CTG CAC CTG ACG ATT CAA GAG ACC GTT CGA GGC TCC GAT AGG CTG GCC CAG GGA 4198

I   A   H   L   R   L   H   Q   I   L   Q   S   N   D   S   R   F       Y       1419
ATT GCC CAT CGC CTG CTG CAC CAA ATT CAA CAG TCC AAC GAC AGT TCC CGA TTC TAT     4258

Q   V   E   F   D   P   T   P   S   V   L   L   L       V   Y   T   G   Y       1439
CAG GTG GAG TTT GAC ACC CCA TCG GTC CTT CTG TCC GTC AGT CCT CGA TTC TAT         4318
```

FIGURE 1F

```
        A   M   F   A   A   A   E   N   K   V   A   V   K   G   *                              1454
       GCC ATG TTT GCT GCA GCT GAA AAC AAG GTC GCT GTC AAG GGC TGA                              4363

CTCCTCCCTGTTGACGAAGTCTCTTTTCTTTAGAGCATTGCCMYKGMTKCCTGGGGCGGCCCCTCATCGCGTCCTC             4442

CTACCGAAACCTTGCCTTTCTCGATTTATCTTTCGCACAGCAGTTCCGATTGGCTGTGTGTTTCACTTTTAGGGAG             4521

AGTCATATTTGATTATTGTATTATTCCATATTCATGTAAACAAAATTTAGTTTTTGTTCTTAATTGCACTCTAAAAG             4600

GTTCAGGAACCGTTATTATAATTGTATCAGAGGCCTATAATGAAGCTTTATACGTGAGCTATATCTATATATAATTC             4679

TGTACATAGCCTATATATTACAGTGAAAATGTAAGCTGTGTTTATTTTATATTAAAATAAGCACTGTGCTAAAAAAAAAAA         4758

AAAAAAAAAAAAGGGCGGCCGC                                                                    4781
```

FIGURE 1G

```
MRP1    MALRGFCSADGSDPLWDWNVTWNTSNPDFTKCFQNTVLVWVPCFYLWACFPFYFLYLSRH
MRP-β   -----------------DVKLTVCEP WNLHSEKMKDIDIGKEYIIPSP------GYRS
                          *       *                  *           *

MRP1    DRGYIQMTPLNKTKTALGFLLWIVCWADLFYSFWERSRGIFLAPVFLVSPTLLGITTLLA
MRP-β   VRERTSTSGTHRDR------------------EDS-------KFRRTRP-----LECQ
           *                              * *         *

MRP1    TFLIQLERRKGVQSSGIMLTFWLVALVCALAILRSKIMTALKEDAQVDLFRDITFYVYFS
MRP-β   DALETAARAEGLS------------LDASMHSQLRILDEEHPK------GKY----HHG
           *   *                    *       *

MRP1    LLLIQLVLSCFSDRSPLFSETIHDPNPCPESSASFLSRITFWWITGLIVRGYRQP-LEGS
MRP-β   LSALKPIRTTSKHQHP------------VDNAGLFSCMTFSWLSSLARVAHKKGELSME
        *                                *    * **  *   *          *

MRP1    DLWSLNKEDTSEQVVPVLVKNWKKECAKTRKQPVKVVYSSKDPAQPKESSKVDANEEVEA
MRP-β   DVWSLSKHESSDVNCRRLERLWQEELNEVG-----------PDAAS--------------
        * *** *      *       *    *                 *

MRP1    LIVKSPQKEWNPSLFKVLYKTFGPYFLMSFFFKAIHDLMMFSGPQ-ILKLLIKFVNDTKA
MRP-β   -------------LRRVVWIFCRTRLILSIVCLMITQLAGFSGPAFMVKHLLEYTQATES
                     * *             *    * *  ****    * *

MRP1    PDWQGYFYTVLLFVTACLQTLVLHQYFHICFVSGMRIKTAVIGAVYRKALVITNSARKSS
MRP-β   NLQYSLLLVLGLLLTEIVRSWSLALTWALNYRTGVRLRGAILTMAFKKILKLKNIKEKS-
            *   *            *       *       * *        * *   *  **

MRP1    TVGEIVNLMSVDAQRFMDLATYINMIWSAPLQVILALYLLWLNLGPSVLAGVAVMVLMVP
MRP-β   -LGELINICSNDGQRMFEAAAVGSLLAGGPVVAILGMIYNVIILGPTGFLGSAVFILFYP
         ** *  *  ***   *         **         ***     *  *     *

MRP1    VNAVMAMKTKTYQVAHMKSKDNRIKLMNEILNGIKVLKLYAWELAFKDKVLAIRQEELKV
MRP-β   AMMFASRLTAYFRRKCVAATDERVQKMNEVLTYIKFIKMYAWVKAFSQSVQKIREEERRI
          *       *   *   ***  * **  *   **  *** **     * ** **

MRP1    LKKSAYLSAVGTFTWVCTPFLVALCTFAVYVTIDENNILDAQTAFVSLALFNILRFPLNI
MRP-β   LEKAGYFQSITVGVAPIVVVIASVVTFSVHMTLGFD--LTAAQAFTVVTFNSMTFALKV
        * *   *       *         ** *    * **        **    **     *

MRP1    LPMVISSIVQASVSLKRLRIFLSHEELEPDSIERRPVKDGGGTNSITVRNATFTWAR---
MRP-β   TPFSVKSLSEASVAVDRFKSLFLMEEVHMIKNK-----PASPHIKIEMKNATLAWDSSHS
         *    *  ***   *       **         *              ***   *

MRP1    ---------------------------------------------SDPP--------
MRP-β   SIQNSPKLTPKMKKDKRASRGKKEKVRQLQRTEHQAVLAEQKGHLLLLDSDERPSPEEEEG
                                                     **

MRP1    -----------TLNGITFSIPEGALVAVVGQVGCGKLSLLSALLAEMDKVEGHVAIKGS
MRP-β   KHIHLGHLRLQRTLHSIDLEIQEGKLVGICGSVGSGKTSLISAILGQMTLLEGSIAISGT
                   ** *  * ** **   * ** ** ** **  *    ** **  **

MRP1    VAYVPQQAWIQNDSLRENILFGCQLEEPYYRSVIQACALLPDLEILPSGDRTEIGEKGVN
MRP-β   FAYVAQQAWILNATLRDNILFGKEYDEERYNSVLNSCCLRPDLAILPSSDLTEIGERGAN
        *** ***** *  ** ***** *   ** ***  * * * **** ***  ***** * *

MRP1    LSGGQKQRVSLARAVYSNADIYLFDDPLSAVDAHVGKHIFENVIGPKGMLKNKTRILVTH
MRP-β   LSGGQRQRISLARALYSDRSIYILDDPLSALDAHVGNHIFNSAIR--KHLKSKTVLFVTH
```

MRP1     SMSYLPQVDVIIVMSGGKISEMGSYQELLARDGAFAEFLRTYASTEQEQDAEENGVTGVS
MRP-β    QLQYLVDCDEVIFMKEGCITERGTHEELMNLNGDYATIFNNLLLG E
              **   *  *   *  * * *       **     *  *

MRP1     GPGKEAKQMENGMLVTDSAGKQLQRQLSSSSSYSGDISRHHNSTAELQKAEAKKEETWKL
MRP-β    ------------TPPVEINS---KKETSGSQKKS--QDKGPK-TGSIKKEKAVKPEEGQL
                                 * *    *           *   *   ****    *

MRP1     MEADKAQTGQVKLSVYWDYMKAIG-LFISFLSIFLFMCNHVSALASNYWLSLWTDDP---
MRP-β    VQLEEKGQGSVPWSVYGVYIQAAGGPLAFLVIMALFMLNVGSTAFSTWWLSYWIKQGSGN
            * *   ***    *   *        ** *  *    *    ***  *

MRP1     ----IVNGTQEHT--------KVRLSVYGALGISQGIAVFGYSMAVSIGGILASRCLHVD
MRP-β    TTVTRGNETSVSDSMKDNPHMQYYASIYALSMAVMLILKAIRGVVFVKGTLRASSRLHDE
             *  *                   * *         *             *   *  **

MRP1     LLHSILRSPMSFFERTPSGNLVNRFSKELDTVDSMIPEVIKMFMGSLFNVIGACIVILLA
MRP-β    LFRRILRSPMKFFDTTPTGRILNRFSKDMDEVDVRLPFQAEMFIQNVILVFFCVGMIAGV
          *  ******  **   *    * ****   *  *   *    **      *       *

MRP1     TPIAAIIIPPLGLIYFFVQRFYVASSRQLKRLESVSRSPVYSHFNETLLGVSVIRAFEEQ
MRP-β    FPWFLVAVGPLVILFSVLHIVSRVLIRELKRLDNITQSPFLSHITSSIQGLATIHAYNKG
          *                  *  ****       **  **    *       *  *

MRP1     ERFIHQSDLKVDENQKAYYPSIVANRWLAVRLECVGNCIVLFAALFAVISRHSLSAGLVG
MRP-β    QEFLHRYQELLDDNQAPFFLFTCAMRWLAVRLDLISIALITTTGLMIVLMHGQIPPAYAG
          * *       *  **           *******                *  *        *

MRP1     LSVSYSLQVTTYLNWLVRMSSEMETNIVAVERLKEYSETEK-EAPWQIQETRPPSSWPQV
MRP-β    LAISYAVQLTGLFQFTVRLASETEARFTSVERINHYIKTLSLEAPARIKNKAPSPDWPQE
          *  **  *      **  ** *     ***   *    ***  *       *    ***

MRP1     GRVEFRNYCLRYREDLDFVLRHINVTINGGEKVGIVGRTGAGKSSLTGLFRINESAEGE
MRP-β    GEVTFENAEMRYRENLPLVLKKVSFTIKPKEKIGIVGRTGSGKSSLGMALFRLVELSGGC
          *  *   *   ****  *  **    *    ** *******  *****  ***   *

MRP1     IIIDGINIAKIGLHDLRFKITIIPQDPVLFSGSLRMNLDPFSQYSDEEVWTSLELAHLKD
MRP-β    IKIDGVRISDIGLADLRSKLSIIPQEPVLFSGTVRSNLDPFNQYTEDQIWDALERTHMKE
          * ***   *   *** *** ***  * ****** *    ****  * *** **       *  **  *

MRP1     FVSALPDKLDHECAEGGENLSVGQRQLVCLARALLRKTKILVLDEATAAVDLETDDLIQS
MRP-β    CIAQLPLKLESEVMENGDNFSVGERQLLCIARALLRHCKILILDEATAAMDTETDLLIQE
          **  **    *  *   *  *** *** *  ******   ***  ******  *  *** ***

MRP1     TIRTQFEDCTVLTIAHRLNTIMDYTRVIVLDKGEIQEYGAPSDLLQQ-RGLFYSMAKDAG
MRP-β    TIREAFADCTMLTIAHRLHTVLGSDRIMVLAQGQVVEFDTPSVLLSNDSSRFYAMFAAAE
          ***   *  ***  *******  *    *  **   *    **  **     **  *

MRP1     LV-----
MRP-β    NKVAVKG
```

FIGURE 2B

MULTIDRUG RESISTANCE-ASSOCIATED POLYPEPTIDE

RELATED APPLICATIONS

This patent application is a divisional of U.S. Ser. No. 08/843,459, entitled "Novel Multidrug Resistance-Associated Polypeptide", filed Apr. 16, 1997, the disclosure of which is incorporated herein by reference.

FIELD OF THE INVENTION

The present invention relates generally to cancer chemotherapy. The invention relates more specifically to compositions and methods for improving the effectiveness of a chemotherapeutic regimen to eradicate multidrug-resistant transformed cells from the body of a mammal, preferably from the body of a human. In this regard, the invention capitalizes on the discovery of a novel multidrug-resistance associated polypeptide (MRP), herein designated MRP-β. The invention further relates to drug discovery, especially to the design of novel chemotherapeutic drugs that are cytotoxic to cells expressing MR-β.

BACKGROUND OF THE INVENTION

Cancer chemotherapy involves the administration of one or more cytotoxic or cytostatic drugs to a cancer sufferer. The goal of chemotherapy is to eradicate a substantially clonal population (colony) of transformed cells from the body of the individual, or to suppress or to attenuate growth of the colony, which is most commonly referred to as a tumor. Tumors may occur in solid or liquid form, the latter comprising a cell suspension in blood or another body fluid. A secondary goal of chemotherapy is stabilization (clinical management) of the afflicted individual's health status. Although the tumor may initially respond to chemotherapy by, e.g., stabilizing or reducing its growth rate, in many instances the initial chemotherapeutic treatment regimen becomes less effective or ceases to impede tumor growth. Conventional treatment regimes endorse the use of additional or substitute chemotherapeutic drugs, including drug combinations, in an effort to regain control over tumor growth. However, it is well known that transformed cells in a tumor may acquire resistance to a broad spectrum of chemotherapeutic drugs, including drugs to which the tumor has not hitherto been exposed during treatment. This acquisition of a multidrug-resistant (or multidrug-resistance) phenotype significantly constrains the chemotherapeutic choices available to the clinician, and significantly worsens prognosis for the afflicted individual. Acquisition of multidrug resistance is particularly problematic in carcinomas originating in secretory epithelia, including lung, gastrointestinal tract, mammary, reproductive tract, endocrine and neuroendocrine epithelia.

Tumor cell transformation is the process by which a cell escapes normal control mechanisms governing the cell's tissue-specific phenotype and differentiation state. Thus, transformation often involves "dedifferentiation," which is defined as an inappropriate return to a less committed or less tissue-specific phenotype. Alternatively, transformation involves incomplete or arrested differentiation of cells normally responsible for replenishing cells lost to normal tissue turnover. Transformed cells of epithelial origin produce tumors that are carcinoma cell colonies (carcinomas). When in a gland-like configuration or derived from secretory tissue, such epithelium-derived tumors are referred to as adenocarcinomas. In contrast, transformed cells of mesenchymal origin produce tumors that are sarcoma cell colonies (sarcomas). Transformed cells of the hematopoietic lineage produce leukemias, lymphomas or lymphosarcomas, each of which often occur as cell suspension tumors. In contrast, the primary tumor growth of a carcinoma or sarcoma usually remains near the site of initial cell transformation. However, secondary foci (metastases) of tumor growth can arise at other sites, which can be far removed from the primary tumor growth site. The presence and/or abundance of metastases indicates the degree to which transformed cells have strayed from their normal tissue-specific phenotype and/or acquired invasive properties.

Phenotypically, cell transformation involves the display of altered or abnormal structural (e.g. antigenic) and functional cellular properties. These altered properties provide the transformed cell with a survival or growth advantage over neighboring, non-transformed cells in its tissue of origin. The advantage may arise from acquisition of autocrine growth regulation, abnormal activation of genes controlling or regulating the cell division cycle, abnormal suppression of genes needed for normal exit from or arrest of the cell division cycle, or other changes affecting cell growth and/or survival. Over time, divisions of the transformed cell produce a colony (tumor) of daughter cells each having the phenotypic advantage gained by the original transformed cell. The imposition of chemotherapy subjects the tumor to selection pressure, in effect encouraging further phenotypic change by which tumor cells may escape the cytotoxic effects of a chemotherapeutic drug. Thus, the structural and functional properties of transformed cells in a tumor can fluctuate over time and over the course of chemotherapeutic treatment.

A significant survival advantage is associated with the acquisition of a multidrug-resistance phenotype, which arises from expression of a cellular gene encoding a protein that removes diverse chemotherapeutic drugs or drug metabolites from the intracellular milieu. Drug export diminishes cytotoxic effect, thereby protecting the transformed cell from otherwise lethal chemotherapeutic drugs or drug concentrations. To date, two genes encoding multidrug-resistance export proteins have been identified in the human genome. The first of these, MDR1, encodes P-glycoprotein, a 170 kDa multispanning transmembrane protein belonging the ATP Binding Cassette (ABC) Transporter protein superfamily. Lautier et al. (1996), 52 *Biochem. Pharmacol.* 967–977. Superfamily members are multispanning tansmembrane proteins that transport substances into or out of the intracellular environment in an energy-dependent manner. Higgins (1992), 8 *Ann. Rev. Cell Biol.* 67–113, provides a general overview of the properties and natural occurrence of superfamily member proteins. ABC transporters have been identified for a large variety of structurally diverse transported substrates, including sugars, peptides, inorganic ions, amino acids, polysaccharides and proteins. Individual transporter proteins appear to function unidirectionally, i.e., to carry out either export or import of intracellular substances. Thus, P-glycoprotein functions by exporting chemotherapeutic drugs which, although structurally heterogenous, appear to share hydrophobic properties. P-glycoprotein overexpression correlates with the presence of a multidrug-resistance phenotype in diverse tumor cell isolates and tumorigenic cell lines. Significant effort has been invested in the development of agents to block or attenuate P-glycoprotein mediated drug export. Such agents are referred to commonly as "chemosensitizers" or "MDR reversal agents," and are disclosed in Hait et al. (1992), U.S. Pat. No. 5,104,858; Sunkara et al. (1993), U.S. Pat. No. 5,182,293; Sunkara et al. (1993), U.S. Pat. No. 5,190,957;

Ramnu et al. (1993), U.S. Pat. No. 5,190,946; Powell et al. (1995), U.S. Pat. No. 5,387,685; Piwnica-Worms (1995), U.S. Pat. No. 5,403,574; Sarkadi et al. (1995), PCT Publication WO 95/31474; Sunkara et al. (1996), U.S. Pat. No. 5,523,304; Zelle et al. (1996), U.S. Pat. No. 5,543,423; Engel et al. (1996), U.S. Pat. No. 5,556,856; Powell et al. (1996), U.S. Pat. No. 5,550,149 and Powell et al. (1996), U.S. Pat. No. 5,561,141. However, P-glycoprotein overexpression does not account for all instances of the acquisition of a multidrug-resistance phenotype. Lautier et al. (1996), 52 *Biochem. Pharmacol.* 967–977.

A second multidrug-resistance gene identified to date in the human genome encodes multidrug-resistance associated protein (MRP), a 190 kDa multispanning transmembrane protein also belonging to the ABC Transporter protein superfamily. MRP is described in Deeley et al. (1996), U.S. Pat. No. 5,489,519, the teachings of which are incorporated by reference herein. MRP shares only 15% sequence identity with P-glycoprotein at the amino acid level. In addition, MRP differs from P-glycoprotein in its ability to expel specific types of chemotherapeutic drugs from the intracellular milieu. These differences are thought to arise from differences in the drug expulsion mechanism of the two proteins: MRP appears to act on a glutathione-derivatized drug metabolite, whereas P-glycoprotein appears to act on an underivatized drug. Lautier et al. (1996), 52 *Biochem. Pharmacol.* 967–977. Significantly, agents that block or interfere with P-glycoprotein function appear to have little crossreactivity with MRP. Thus, significant effort is being invested in the development of substances (MDR reversal agents) that block or inhibit MRP function.

Overexpression of either P-glycoprotein or MRP can endow a transformed cell with a multidrug-resistance phenotype; thus, empirical testing is required to determine whether a particular reversal agent will be effective for interfering with a tumor's multidrug resistance phenotype. Currently, it is unclear whether MRP and/or P-glycoprotein expression accounts for all occurrences of the multidrug-resistance phenotype, which arises fairly commonly during the course of chemotherapeutic treatment, irrespective of the tissue specificity of the primary tumor. Moreover, the expression patterns of MRP and P-glycoprotein within a given cell population have been observed to fluctuate over time. Thus, exposure to a reversal agent that interferes with P-glycoprotein function may impose selection pressure favoring the expression of MRP. Such pressure would result in continued viability of cells having a multidrug resistance phenotype. Lautier et al. (1996), 52 *Biochem. Pharmacol.* 967–977.

Needs remain for preventing or reversing the acquisition of a multidrug resistance phenotype in transformed cells. Particular needs remain to establish the mechanism(s) by which the multidrug resistance phenotype can be produced, and to provide additional therapies for restoring drug sensitivity to multidrug-resistant transformed cells. Still more particular needs remain to improve the clinical management of multidrug resistant tumors, especially when the multidrug resistance phenotype arises entirely or partially from overexpression of one or more genes other than those encoding P-glycoprotein or MRP.

SUMMARY OF THE INVENTION

The present invention capitalizes on the unexpected discovery of a novel gene encoding a hitherto-unknown multidrug-resistance associated polypeptide (MRP). This novel polypeptide, designated herein as MRP-β, is encoded in the human genome and is expected to be found in the genomes of additional mammals. MRP-β likely is a transmembrane-spanning, energy-dependent transporter or pump, as are other members of the ATP Binding Cassette (ABC) Transporter Protein superfamily to which the known proteins MRP and P-glycoprotein belong. It is likely that MRP-β is disposed in the plasma membrane of a mammalian cell, and functions by ejecting intracellular substances, such as chemotherapeutic drugs. Alternatively, MRP-β may span a vesicular membrane, and function by sequestering intracellular substances. Elevated levels of expression of the novel MRP-β gene, or of bioactivity of the novel MRP-β polypeptide encoded by this gene, accordingly are expected to contribute to the emergence and/or persistence of a multidrug-resistance phenotype in transformed mammalian cells, such as carcinoma cells, including adenocarcinoma cells. Elevated expression or bioactivity of MRP-β similarly is expected to contribute to the occurrence of a multidrug-resistance phenotype in sarcoma cells and in transformed cells of the hematopoietic lineage, including leukemias, lymphomas and lymphosarcomas. MRP-β is likely to account for multidrug-resistant mammalian cell phenotypes that are refractory to treatment with reversal agents that interfere with expression, production and/or function of P-glycoprotein or of MRP.

Accordingly, it is an object of this invention to provide nucleic acids and expression vectors encoding MRP-β or a unique fragment thereof. It is another object to provide nucleic acids, including probes and antisense oligonucleotides, complementary to MRP-β encoding nucleic acids. An additional object is to provide methods and compositions for mitigating aberrant expression of an MRP-β gene, or for mitigating aberrant bioactivity of an MRP-β polypeptide. It is yet another object to provide methods and compositions for characterizing and/or attenuating a multidrug resistance phenotype. It is still another object to provide methods and compositions, including MRP-β expressing host cells, for identifying one or more modulators, preferably inhibitors, of MRP-β. A still further object includes the modulation, preferably the inhibition, of MRP-β and of disease states associated with MRP-β. A yet further object includes the potentiation of chemotherapy to eradicate multidrug resistant transformed cells from the body of an individual, such as a cancer patient. These and other objects, along with advantages and features of the invention disclosed herein, will be apparent from the description, drawings and claims that follow.

In a first aspect, the invention features nucleic acids encoding or complementary to MRP-β or a unique fragment thereof. A preferred embodiment provides nucleic acid, the sequence of which comprises SEQ ID No: 1, an MRP-β cDNA sequence. Another preferred embodiment provided MRP-β cDNA deposited on even date herewith, under the terms of the Budapest Treaty, with the American Type Culture Collection (ATCC), 12301 Parklawn Drive, Rockville, Md. 20852. The deposited cDNA is herein designated fohd013a05m and is accorded Deposit No. 98409 Another preferred embodiment provides ribonucleic acid (RNA) encoding an MRP-β polypeptide, the amino acid sequence of which comprises SEQ ID No: 2. Messenger RNA (mRNA) encoding MRP-β is approximately 6 kilobases (kb) in length. Other embodiments provide unique fragments (e.g., SEQ ID No: 3) of the MRP-β cDNA, including fragments corresponding to portions of the open-reading frame (ORF), and fragments corresponding to untranslated sequences 3' or 5' to the ORF. These unique fragments can be used to produce or design probes for the analysis of cellular MRP-β expression patterns, e.g., for purposes of diagnosing an abnormality in or contributed to by MRP-β. In addition, the present fragments can be used for the production or design of polymerase chain reaction (PCR) primers or antisense oligonucleotides, including therapeutic oligonucleotides that disrupt cellular MRP-β gene expression, especially abnormal or aberrant expression. It will be understood that the present nucleic acids, especially probes and oligonucleotides, may be detectably labelled and/or may comprise one or more modifications in a nucleotide base, backbone sugar or phosphate, or be linked together by linkages other than phosphodiester bonds.

The invention is further embodied in nucleic acids that hybridize to SEQ ID No: 1 or to the complement thereof. Preferred nucleic acids hybridize to SEQ ID No: 1 or to the complement thereof under stringent conditions. Preferred antisense and/or primer oligonucleotides hybridize to unique fragments of SEQ ID No: 1 or of the complement thereof, e.g., under intracellular conditions. Additional MRP-β variant nucleic acids provided herein comprise nucleotide sequences at least 50%, preferably 60%, 70%, 80%, more preferably 90% and even more preferably 95% identical to SEQ ID No: 1. The present variant nucleic acids comprise nucleotide mutations (substitutions, deletions and/or insertions) distributed in any random or non-random frequency within the SEQ ID No: 1 sequence. The invention further provides degenerate variant nucleic acids that encode the SEQ ID No: 2 polypeptide or a unique fragment thereof. In yet further embodiments, the invention provides nucleic acids encoding variant MRP-β polypeptides, comprising amino acid sequences sharing at least 75% sequence similarity With the SEQ ID No: 2 polypeptide. Preferably, these nucleic acids encode polypeptides sharing at least 80%, 85%, 90% or more preferably 95% amino acid sequence similarity with the SEQ ID No: 2 MRP-β polypeptide. The encoded variant polypeptides comprise amino acid mutations (substitutions, deletions and/or insertions) distributed in any random or non-random frequency within the SEQ ID No: 2 sequence. "Similarity" as used herein refers to the sum of aligned amino acid residues that are identical to the corresponding SEQ ID No: 2 residues and those that are allowed point mutations therefor. Moderate gaps and/or insertions (e.g., less than about 50, preferably less than about 15, more preferably less than about 5 amino acid residues) in the aligned sequence are ignored for similarity calculation purposes. Allowed point mutations are substitutions by amino acid residues that are physically and/or functionally similar to the corresponding aligned SEQ ID No: 2 residues, e.g., that have similar size, shape, hydrophilic or hydrophobic character, charge and chemical properties.

It should be understood that the present invention provides oligonucleotides that hybridize to any of the foregoing variant MRP-β nucleic acids, i.e., to nucleic acids that encode polypeptides comprising amino acid sequences that share at least 75% sequence similarity with the SEQ ID No: 2 polypeptide. More particularly, the invention provides olignucleotides that hybridize to one or more unique fragments of nucleic acids encoding the present MRP-β polypeptides. For therapeutic purposes and/or for PCR investigative or diagnostic purposes, the present oligonucleotides hybridize to a unique fragment comprising 5' untranslated sequence, a transcription initiation site, ORF or polypeptide coding sequence, intron-exon boundary, polyadenylation site or 3' untranslated region of the present MRP-β nucleic acids. Exemplary antisense oligonucleotides are disclosed herein (SEQ ID Nos: 4, 5, 6, 7 and 8).

For antisense-oligonucleotide based therapeutic purposes, one or more of the present antisense MRP-β oligonucleotides (optionally comprising one or more modified moieties as disclosed herein) is formulated together with a pharmaceutically acceptable -vehicle to produce an antisense pharmaceutical composition suitable for local or systemic administration to a mammal, or for treatment of mammalian cells or tissue whether in situ or ex vivo. In an alternative embodiment, the present antisense oligonucleotide is encoded by an antisense expression vector comprising a nucleic acid insert complementary to the oligonucleotide sequence. The antisense vector preferably comprises or is packaged with one or more retroviral elements for infection of mammalian cells, and further comprises one or more conventional expression control elements (e.g., a promoter, transcriptional initiation site, termination site, or the like) to direct intracellular production of the antisense oligonucleotide in infected cells. The present vector also can be formulated with a pharmaceutically acceptable vehicle to produce additional antisense pharmaceutical compositions of the present invention. Thus, the antisense vector, when internalized by a cell (e.g., by retroviral infection, pinocytosis or diffusion), directs the intracellular production of an antisense oligonucleotide which, as do any of the therapeutic antisense oligonucleotides disclosed herein, disrupts cellular expression of an MRP-β gene. Disruption of expression is achieved by interfering with MRP-β gene activation or transcription, by destabilization of MRP-β gene transcripts, or by interference with the translation of MRP-β gene transcripts. In this manner, the present invention provides compositions for mitigating aberrant expression of an MRP-β gene, e.g., expression which contributes to the emergence or persistence of a multidrug-resistant phenotype.

In a second aspect, the invention features an MRP-β polypeptide, the amino acid sequence of which comprises SEQ ID No: 2. More generally, the invention provides MRP-β polypeptides, and unique fragments (epitopes) thereof, that are encoded by any of the above-described MRP-β nucleic acids. For example, the invention provides MRP-β polypeptides, the amino acid sequences of which comprise a sequence sharing at least 75% sequence similarity (as defined herein) with SEQ ID No: 2. Such MRP-β polypeptides include naturally-occurring variants (e.g., polymorphic variants, phylogenetic counterparts of the presently disclosed human MRP--β, and/or naturally-occurring mutant variants, particularly mutants associated with the process of somatic cell transformation or tumorigenesis) and biosynthetic variants produced by routine molecular engineering techniques. Based upon an assessment of its sequence similarity to known proteins, such as MRP, the present novel MRP-β polypeptide is believed to be a novel member of the ABC Transporter Protein superfamily. Thus, it is anticipated that MRP-β polypeptides will be displayed on the surface of cells expressing an MRP-β gene, such as multidrug resistant tumor cells or transfected host cells. Of course, it is also possible that MRP-β will be incorporated into intracellular phospholipid membranes, such as vesicular membranes. Cellular production of MRP-β is expected to contribute to the emergence and/or persistence of a multidrug-resistant phenotype in transformed mammalian cells. The present invention provides various specific MRP-β polypeptide embodiments, including MRP-β polypeptides immunogenically displayed on intact host cell membranes or cell-free membrane fractions derived from host cells; MRP-β polypeptides incorporated into synthetic or non-cellular phospholipid membranes or micelles, and MRP-β polypeptides and polypeptide fragments isolated in substantially pure form. Any of the foregoing polypeptides, or unique, immunogenic fragments (epitopes) thereof can be used to induce immune responses in human or nonhuman mammals.

Accordingly, in a third aspect, the invention features an antibody that binds selectively to an epitope unique to MRP-β. Preferably, the invention provides an antibody that binds to an MRP-β epitope that is displayed on the surface of MRP-β expressing cells, such as transformed or host cells. Antigen-binding fragments of the present antibody also are provided herein. Such fragments include truncated forms of the antibody that retain antigen binding properties, e.g., Fab, $Fab_2$, Fab' and Fv fragments thereof. Such fragments are produced conventionally by enzymatic or chemical cleavage of an intact antibody of the present invention. Alternatively, such fragments can be produced through molecular engineering techniques. In certain embodiments, the present antigen binding fragment is incorporated into a fusion polypeptide, such that the fragment is fused to another polypeptide, such as an immunoglobulin framework polypeptide. An exemplary framework is of human origin. Alternatively, the antigen-binding region is fused to a non-immunoglobulin polypeptide, e.g., to a cytotoxin or to a chemoattractant polypeptide. A cytotoxin polypeptide induces or mediates cell death (cytolysis), e.g., by inducing apoptosis or by disrupting cell metabolism, cell membrane integrity, intracellular fluid volume, or the like. Exemplary cytotoxic fusion proteins comprise ricin, diptheria toxin, or another naturally-sourced toxin of plant, animal or microbial origin. A chemoattractant polypeptide is any polypeptide of mammalian origin that induces or stimulates activation and localization of immune effector cells (e.g., natural killer cells, cytotoxic T cells, macrophages and the like) that typically mediate a cellular proinflammatory immune response. Exemplary chemoattractant fusion proteins comprise a chemokine, lymphokine or cytokine polypeptide (e.g., interleukin-2 (IL2), tumor necrosis factor (TNF), and the like).

In a fourth aspect, the invention features expression vectors comprising nucleic acid encoding an MRP-β polypeptide comprising an amino acid sequence that shares at least 75% sequence similarity with SEQ ID No: 2. The nucleic acid sequence of an exemplary expression vector thus comprises SEQ ID No: 1. The nucleic acid sequence of another exemplary expression vector comprises the sequence of MRP-β cDNA deposited on even date herewith. Additional exemplary expression vectors comprise nucleic acid encoding variants, whether biosynthetic or naturally-sourced, of the presently disclosed MRP-β polypeptide Certain embodiments of the present expression vectors encode chimeric polypeptides in which one or more MRP-β amino acid residues are substituted by the corresponding residues of another ABC Transporter Protein superfamily member, such as MRP or P-glycoprotein. Such embodiments are expected to facilitate elucidation of the molecular basis of multidrug resistance phenotypes, and thence to facilitate design or screening of novel inhibitors of multidrug resistance. In addition to nucleic acid encoding the MRP-β polypeptide, the present expression vectors comprise one or more expression control elements (e.g., promoter, transcriptional initiation site, termination site and the like) to direct the production of the encoded MRP-β polypeptide in prokaryotic or, preferably eukaryotic, host cells. Optionally, the present expression vectors further comprise a selectable marker gene. For use with eukaryotic host cells, the present expression vector may still further comprise one or more retroviral components to promote infectivity and uptake by eukaryotic, preferably mammalian, cells.

Accordingly, a fifth aspect of the present invention features a host cell transfected with an above-described expression vector. A preferred host cell displays a vector-encoded MRP-β polypeptide, comprising a sequence sharing at least 75% sequence similarity with SEQ ID No: 2, on the cell surface. A particularly preferred host cell displays a functional and immunologically detectable MRP-β polypeptide. In other embodiments the vector encoded MRP-β polypeptide may reside within the cell, e.g., as a component of a vesicular membrane. Preferred host cells acquire a multidrug resistance phenotype and are able to eject or sequester intracellular substances, including chemotherapeutic drugs and/or metabolites thereof. The present host cells can be of human or non-human origin, and can be naturally-sourced, adapted to primary culture, or immortalized under culture conditions. Cells that are suitable for production of host cells are herein defined as source cells. Exemplary source cells include normal differentiated mammalian cells (e.g., obtained by biopsy), cells in primary culture (e.g., serially passaged benign or malignant transformed cells), and cell lines (e.g., immortalized transformed cells such as HeLa, MCF-7, and the like). Preferably, mammalian source cells are primate cells, most preferably human cells. For screening or other investigative purposes, such as the production of non-human mammals, rodent, ovine, porcine, bovine or other mammalian source cells may be used. In other embodiments, host cells can be produced from prokaryotic or eukaryotic source cells, e.g., unicellular organisms, such as yeast. Any of the foregoing can be used to produce host cells by standard cell transfection or infection techniques. Thus, an MRP-β expression vector can be stably incorporated into a source cell by transfection, pinocytosis, electroporation, microinjection, retroviral infection or the like. Transfected cells then are cultured under conditions favorable to the selective survival of MRP-β expressing host cells, e.g., in the presence of a drug cytotoxic to source cells but to which expression of MRP-β or a vector-borne selectable marker gene confers a survival advantage for host cells. Host cells so obtained are useful for the production and characterization of MRP-β antibodies, for investigation of the nature and variety of toxic substances subject to MRP-β transport, and for the screening and identification of MRP-β inhibitors as described herein.

In further embodiments, MRP-β host cells can be produced from uncommitted source cells, preferably embryonic stem cells or blastocyst cells, of non-human mammalian origin. An uncommitted cell is one that is competent to differentiate, under appropriate conditions, into differentiated cells of one or more specific mammalian body tissues. In the present embodiment, an MRP-β expression vector is introduced into an uncommitted embryonic source cell and preferably integrates in a site-specific or nonspecific fashion into the cells' genome to produce a host cell competent to differentiate into one or a plurality of differentiated cell types. Alternatively, the present expression vector resides in the host cell as microsatellite DNA. In some embodiments, the present expression vector confers a tissue-specific pattern of MRP-β expression in tissue arising from the differentiation of uncommitted host cells. Uncommitted host cells can, through manipulation by established techniques, be used to produce non-human mammals that are either transgenic or nullizygous for MRP-β. To produce a transgenic mammal of the present invention, an above-described host embryonic stem cell or blastocyst cell is integrated (e.g., by microinjection) into a non-human mammalian blastocyst, which is thereafter implanted into the uterus of a non-human, pseudopregnant mammal, such as a mouse, rat, rabbit, sheep, goat, pig or cow. Following a normal gestation period, this intrauterine implantation procedure yields a non-human founder mammal, the body tissues of which comprise a mosaic of normal cells and host cells, the latter comprising MRP-β nucleic acid of vector origin. Progeny of the present founder mammal are characterized by germline integration of nucleic acid of vector origin. Transgenic progeny express an MRP-β polypeptide, the amino acid sequence of which comprises a sequence sharing at least 75% sequence similarity with SEQ ID No: 2. Optionally, this polypeptide is expressed in a tissue-specific manner. Thus, transgenic progeny constitutively or inducibly express MRP-β in all or a subset of their body tissues. Cells isolated or, optionally immortalized from, such transgenic tissue are expected to facilitate investigations into the discovery and characterization of MRP-β modulators useful for treatment of multidrug-resistant transformed cells arising in any mammalian body tissue. For example, transgenic progeny and/or their cells can be used to confirm whether substances initially identified as modulators in an in vitro screen suppress MRP-β polypeptide production or biological function in vitro. Advantageously, transgenic progeny provide a tissue source that can be matched to a tissue type for which modulators of multidrug resistance are particularly desired, e.g., which has a known propensity for developing multidrug resistance. Such tissue types include, but are not limited to, mammary, respiratory tract, gastrointestinal tract, urogenital tract, hematopoietic and endocrine system tissue.

To produce a nullizygous mammal of the present invention, an above-described uncommitted source cell is transfected (e.g., infected) with a null vector, which comprises a non-expressible variant of the MRP-β encoding nucleic acid disclosed herein. The null vector further comprises sufficient nucleic acid sequence 5' and 3' to the MRP-β ORF to achieve homologous recombination with any endogenous MRP-β gene present in the source cells' genome. As a result of homologous recombination, any endogenous MRP-β gene is nullified, i.e., replaced by the present non-expressible variant. Appropriate non-expressible variants include antisense-oriented MRP-β nucleic acids, nucleic acids comprising premature stop codons in the ORF, nucleic acids comprising a defective promoter, and the like. The present null host cell is integrated into a blastocyst and implanted into a pseudopregnant mammal to produce a null founder mammal. Progeny of this founder are characterized by germline integration of nucleic acid derived from the null vector. Thus, in nullizygous progeny, the ability to express a naturally encoded MRP-β homolog is "knocked out" such that, preferably, the progeny are incapable of developing a multidrug resistance phenotype attributable to MRP-β expression. Such nullizygous progeny and/or their cells can be used to assess potential side effects or undesirable consequences of MRP-β modulator (e.g., inhibitor) therapy. Nullizygous progeny and/or their cells also can be used to detect additional genes that contribute to emergence of a multidrug-resistance phenotype, i.e., genes other than MRP-β, MRP and P-glycoprotein. Cells isolated or cultured from nullizygous progeny can be exposed to selection pressure by culturing them in the presence of a chemotherapeutic drug, and monitoring the cultures for emergence of a drug-resistant phenotype. Optionally, the MRP-β nullizygous progeny provided herein can be cross-bred with non-human mammals nullizygous for MRP and/or P-glycoprotein. Such multiply nullizygous progeny should facilitate screening for additional genes that can contribute to the emergence of a multidrug resistance phenotype.

The above-described MRP-β compositions are useful according to teachings herein for assessing the presence of mutations in an MRP-β gene; assessing MRP-β gene expression level, especially for detecting fluctuations in expression; and, for mitigating aberrant expression and/or biological function of an MRP-β polypeptide. Preferably, the present MRP-β compositions are useful to treat a disease state or other deleterious condition contributed to by aberrant MRP-β gene expression or biological function. Most preferably, the present MRP-β compositions are useful to attenuate and/or to abrogate a multidrug resistant phenotype, e.g., of transformed cells in the body of a cancer sufferer. As a result, the present invention offers means for potentiating chemotherapy to eradicate multidrug-resistant transformed cells from an individual's body.

Thus, in a sixth aspect, the invention features diagnostic methods for detecting abnormalities in an MRP-β gene. In one embodiment, the invention provides a method of detecting a mutation or other structural abnormality in an MRP-β gene. Mutations, whether of germline or somatic origin, may indicate whether the process of cell transformation (tumorigenesis) has been initiated or is likely to arise in an individual's tissues. Mutations are detected by obtaining cellular tissue from a mammal, preferably a human, suspected of harboring a variant MRP-β gene, and treating the tissue so as to release nucleic acids therefrom. Preferably the cellular tissue is obtained from a body tissue suspected of comprising transformed cells. Thus, the present method provides information relevant to diagnosis of the presence of a tumor. The method may be practiced with any body tissue type which comprises cells, including body fluid cell suspensions (e.g., blood, lymph, cerebrospinal fluid, peritoneal fluid or ascites fluid). Released cellular nucleic acids are combined, under hybridization conditions, with an oligoucleotide of the present invention, e.g., an oligonucleotide complementary to nucleic acid encoding MRP-β. Preferably, the oligonucleotide is complementary to a unique fragment of the full-length MRP-β nucleic acid. Following incubation with the oligonucleotide under suitable hybridization conditions, the released nucleic acids are assayed for formation of a hybrid comprising the oligonucleotide. In a preferred embodiment wherein the oligonucleotide is complementary to SEQ ID No: 1 or a unique fragment thereof, formation of the hybrid confirms that the individual harbors at least one wild-type MRP-β gene allele (comprising SEQ ID No: 1). Failure to form a hybrid under stringency conditions that do not tolerate base pair mismatching confirms that the individual lacks a wild-type allele, i.e., that the individual harbors an aberrant, e.g., mutant, variant of the MRP-β gene.

In another embodiment, the invention provides a method of assessing expression, especially aberrant expression, of a cellular MRP-β gene. As with the preceding embodiment, aberrant expression may indicate the presence, persistence or reappearance of multidrug-resistant tumor cells in an individual's tissue. More generally, aberrant expression may indicate the occurrence of a deleterious or disease-associated phenotype contributed to by MRP-β. MRP-β gene expression is assessed by obtaining a sample of cellular tissue from a mammal (e.g., a human), preferably from a body site implicated in a possible diagnosis of diseased or malignant tissue, and treating the tissue to release RNA therefrom. Cellular RNA is combined with an MRP-β oligonucleotide generally as described above, and the resulting mixture is assayed for the presence of a hybrid comprising the MRP-β oligonucleotide and a cellular MRP-β gene transcript. In preferred embodiments, the presence and/or relative abundance of this hybrid is expected to indicate aberrant expression of a cellular MRP-β gene, and to correlate with the occurrence in situ of transformed cells, especially transformed cells having a multidrug-resistant phenotype.

Preferably, the foregoing embodiments can be practiced using a detectably labeled or otherwise modified MRP-β oligonucleotide, most preferably with an oligonucleotide comprising a peptide-nucleic acid backbone.

In yet another embodiment, the invention provides a diagnostic method using an above-described antibody or fragment thereof to characterize aberrant MRP-β associated phenotype, e.g., drug-resistant phenotype of a transformed cell. This method involves obtaining cellular tissue from a mammal (e.g., a human) suspected of harboring transformed cells, and contacting the tissue with an above-described antibody under conditions such that, if cells of the obtained tissue display a recognized epitope unique to MRP-β, an antibody-epitope complex forms. Generally, the method is practiced with intact cells. The practitioner may, however, desire to generate a more sensitive assay for total cellular MRP-β content. In these circumstances, the method is practiced with permeabilized or solubilized cells, which can be produced by exposing the cells to heat, mechanical disruption, detergent, hypo- or hyper-osmotic conditions, and like conventional techniques. After a sufficient period of time has elapsed for formation of the antibody-epitope complex, the tissue is assayed for presence of the complex, formation or abnormal elevation of which indicates presence in the tissue of cells abnormally expressing MRP-β. As disclosed herein, such cells are likely transformed cells characterized by a drug-resistance phenotype.

Information obtained from practice of the foregoing diagnostic methods is expected to be useful in prognostication, staging and clinical management of diseases and other deleterious conditions affecting an individual's health status. In preferred embodiments, the foregoing diagnostic methods provide information useful in prognostication, staging and management of malignancies (tumors) that are characterized by expression of MRP-β and thus by a multidrug-resistance phenotype. The information more specifically assists the clinician in designing chemotherapeutic or other treatment regimes to eradicate such malignancies from the body of an afflicted mammal, typically a human. The present methods can be practiced with any samples of any body tissue type, and are desirable for assessing cellular tissue of mammary, respiratory tract, urogenital tract, endocrine system or immune system origin. The present methods are particularly useful to assess breast biopsy, bronchoalveolar lavage, ovarian, uterine or cervical biopsy, prostate or testicular biopsy, pancreatic biopsy, and spleen, bone marrow or lymph node biopsy samples.

Further general aspects of the invention feature therapeutic methods and compositions, including one or more modulators (stimulators or, preferably, inhibitors) of the expressed MRP-β gene and/or protein. Accordingly, the invention provides means for mitigating (detectably decreasing or otherwise affecting) aberrant expression of an MRP-β gene, or aberrant production or biological function of an MRP-β polypeptide. The invention thus provides means for attenuating an undesirable phenotype, such as a disease-associated phenotype, that is contributed to by MRP-β. In preferred embodiments, the invention provides means for attenuating a multidrug-resistance phenotype, particularly a phenotype contributed to by MRP-β. More particularly, a seventh aspect of the invention features methods for mitigating aberrant expression of an MRP-β gene, and/or aberrant alteration or biological function of an MRP-β polypeptide. One embodiment involves the administration of an antisense pharmaceutical composition of the present invention to a mammal suffering from effects of the aberrant phenotype associated with altered expression and/or function of MRP-β. Another embodiment involves the administration of an antibody or fusion polypeptide of the present invention. In either embodiment, the therapeutic agent is administered systemically or locally under conditions sufficient to mitigate or attenuate the aberrant MRP-β associated phenotype. Preferably, the therapeutic agent is administered under conditions sufficient to destroy cells aberrantly producing MRP-β. In this manner, the invention provides means for destroying multidrug-resistant tumor cells in situ in the body of a mammal. In preferred embodiments, either of the foregoing therapeutic agents can be administered as an adjuvant to conventional chemotherapy. That is, either of the foregoing therapeutic agents can be coadministered together with one or more chemotherapeutic drugs. The present antisense or fusion polypeptide therapeutic agent can be administered prior to, concomitant with, or following administration of one or more chemotherapeutic drugs. In such embodiments, the antisense pharmaceutical composition mitigates resistance of MRP-β expressing cells to the cytotoxic effects of the chemotherapeutic drug. That is, the antisense composition attenuates the MRP-β phenotype, which is expected to be characterized by display of an ABC Transporter Protein family member (MRP-β) and by the property of multidrug resistance. This is accomplished by disrupting activation or transcription of the MRP-β gene, or by destabilizing RNA transcripts thereof. Diminished or discontinued expression of MRP-β renders cells more susceptible to the cytotoxic effects of a chemotherapeutic drug that otherwise would be exported by MRP-β. Similarly, a therapeutically administered cytotoxic fusion polypeptide localizes in the vicinity of cells aberrantly displaying MRP-β, producing cytolysis thereof. A chemoattractant fusion polypeptide also localizes to MRP-β displaying cells, stimulating destruction thereof by macrophages, killer T cells or cytotoxic T cells.

An eighth aspect of the invention features methods for identifying a modulator (a stimulator or, preferably, an inhibitor) of MRP-β. The present modulator is useful for treating a disease or deleterious condition that is contributed to by MRP-β. Preferably, the modulator is a small molecule. In general, the present identification method relies on the use of an MRP-β expressing host cell produced as described herein. Prokaryotic or eukaryotic host cells can be used for purposes of identifying an MRP-β modulator; however in general, eukaryotic host cells are preferred. Yeast or mammalian cells may be used, as desired or as dictated by specific circumstances. Presently, mammalian host cells, particularly human cells are preferred. The MRP-β expressing host cell is contacted with a candidate modulator, and after a sufficient period of time for modulatory effects to be manifested, the cell is assayed to determine whether the candidate indeed affects MRP-β. In one embodiment, the level of cellular MRP-β gene expression is assayed. A detectable decrease (attenuation) or cessation (abrogation) in MRP-β gene expression indicates that the candidate is an inhibitory modulator or inhibitor. Conversely, a detectable increase (augmentation) in MRP-β gene expression indicates that the candidate is a stimulatory modulator or stimulator. Another embodiment involves assay of the amount or rate of production of MRP-β polypeptide displayed by the cell. A detectable decrease or cessation of immunologically recognized MRP-β polypeptide indicates that the candidate is an inhibitory modulator. In a third embodiment, the host cell is contacted with a substrate (e.g., a cytotoxin) exported or sequestered by MRP-β. The candidate inhibitor is contacted with the host cell prior to, concomitantly with, or following exposure to the substrate. The amount of substrate exported or sequestered by the cell is assessed. A detectable decrease in efflux or sequestration of the substrate indicates that the candidate is an inhibitory modulator. Alternatively, in specific embodiments wherein the substrate is cytotoxic, survival of the host cell is assessed. A detectable decrease in survival indicates that the candidate is an inhibitory modulator. Candidate substances appropriate for screening as MRP-β modulators in any of the foregoing embodiments include natural or synthetic metabolites, toxins, antibiotics, elements of a combinatorial chemistry, nucleotide or peptide library, naturally sourced cell secretion products, cell lysates, and the like. Preferred substances for screening, and preferred modulators, are small molecules.

Accordingly, a ninth aspect of the invention features an MRP-β modulator, especially an inhibitory modulator, identified by any of the above-described methods. Preferably, the modulator is a small molecule, e.g., an element of a combinatorial chemistry library or a low molecular weight natural or synthetic product or metabolite. The modulator may be dispersed in a pharmaceutically acceptable vehicle to produce a multidrug-resistance attenuating pharmaceutical composition of the present invention.

A tenth aspect of the invention thus features modulator-based methods of mitigating aberrant MRP-β expression and/or polypeptide production and/or biological function. The present method involves the step of administering an MRP-β modulator, optionally dispersed in a pharmaceutically acceptable vehicle to a mammal suffering from effects of the MRP-β associated aberrancy. Therapeutic modulation (preferably inhibition) of MRP-β is useful for the treatment, including prophylaxis, remediation and palliation, of any disease or deleterious condition that is contributed to by abnormality affecting the MRP-β gene, its expression, MRP-β polypeptide production or biological function. In a preferred embodiment, the invention provides a method for improving (potentiating) effectiveness of chemotherapy to eradicate aberrant MRP-β expressing cells, e.g., multidrug resistant transformed cells, from the body of a mammal. This method involves the steps of administering a chemotherapeutic drug to the mammal, and coadministering an MRP-β modulator identified as described herein. Preferably, the modulator is provided in the form of a multidrug-resistance attenuating composition, i.e., dispersed in a pharmaceutically acceptable vehicle. This method is particularly preferred where a chemotherapy adjuvant is desired to eradicate multidrug-resistant tumor cells. Advantageously, the method can be practiced where a fluid (e.g., leukemia, lymphoma, lymphsarcoma or ascites) tumor is present, or where the situs of a primary or metastatic tumor is deemed unsuitable for surgical intervention or especially where a remontant or reemergent tumor is observed following an initial course of chemotherapeutic treatment. The present embodiments are suitable for the treatment of any tumor, especially of mammary, respiratory tract, urogenital tract, endocrine system or immune system origin.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

FIGS. 1A–1G are a text representation of an MRP-β cDNA sequence and of the polypeptide sequence encoded therein, as set forth in SEQ ID Nos: 1 and 2.

FIGS. 2A and 2B are a text representation comprising aligned amino acid sequences of the known ABC Transporter Protein superfamily member MRP (described in Deeley et al. (1996) U.S. Pat. No. 5,489,519), and of the novel MRP-β disclosed herein. Dashes (-) indicate gaps introduced to maximize alignment of similar sequences; asterisks (*) indicate the locations of identical aligned amino acid residues.

DETAILED DESCRIPTION OF PREFERRED EMBODIMENTS

Mammalian cells having a "multidrug-resistance" or "multidrug-resistant" phenotype are characterized by the ability to sequester, export or expel a plurality of cytotoxic substances (e.g., chemotherapeutic drugs) from the intracellular milieu. Cells may acquire this phenotype as a result of selection pressure imposed by exposure to a single chemotherapeutic drug (the selection toxin). Alternatively, cells may exhibit the phenotype prior to toxin exposure, since the export of cytotoxic substances may involve a mechanism in common with normal export of cellular secretion products, metabolites, and the like. Multidrug resistance differs from simple acquired resistance to the selection toxin in that the cell acquires competence to export additional cytotoxins (other chemotherapeutic drugs) to which the cell was not previously exposed. For example, Mirski et al. (1987), 47 *Cancer Res.* 2594–2598, describe the isolation of a multidrug-resistant cell population by culturing the H69 cell line, derived from a human small cell lung carcinoma, in the presence of adriamycin (doxorubicin) as a selection toxin. Surviving cells were found to resist the cytotoxic effects of anthracycline analogs (e.g., daunomycin, epirubicin, menogaril and mitoxantrone), acivicin, etoposide, gramicidin D, colchicine and Vinca-derived alkaloids (vincristine and vinblastine) as well as of adriamycin. Similar selection culturing techniques can be applied to generate additional multidrug-resistant cell populations.

The functional property of multidrug-resistance is associated with expression and cell-surface display of one or more ABC Transporter Protein superfamily members with energy-dependent export function (e.g., P-glycoprotein, MRP or MRP-β as disclosed herein). The cell population described in Mirski et al. (1987) was reported in Cole et al. (1992), 258 *Science* 1650–1654 to overexpress MRP (a correction of the reported MRP sequence appears at 260 *Science* 879). Currently, antibodies specifically reactive with P-glycoprotein or MRP, or nucleic acid probes specific for the corresponding expressed nucleic acid sequences, are used to ascertain the molecular basis of multidrug-resistance in a given cell population. Where the cell population in question includes transformed cells in the body of a cancer sufferer, determination of the molecular basis of the observed phenotype can assist the clinician in ascertaining whether treatment with one of the so-called "chemosensitizers" or "MDR reversal agents," the majority of which affect P-glycoprotein, is appropriate. Thus, knowledge of the molecular basis of the observed phenotype provides information relevant to developing or revising a course of disease management. Zaman et al. (1993), 53 *Cancer Res.* 1747–1750, cautions, however, that the induction or overexpression of MRP does not account for all forms of multidrug-resistance phenotype that are not attributable to P-glycoprotein expression. The discovery of MRP-β, reported herein, establishes that additional members of the ABC Transporter Protein family exist in the mammalian (e.g., human) genome and likely contribute to the occurrence of multidrug-resistance in transformed cells.

MRP-β was identified by computer-assisted screening of a nucleic acid sequence database corresponding to a human endothelial cell cDNA library. The library comprises cDNAs derived from RNA transcripts of genes expressed by differentiated endothelial cells cultured from microvascular tissue of mammary origin. The library was constructed, and nucleic acid components thereof were sequenced, by conventional techniques as set forth in *Current Protocols in Molecular Cloning*, Ausubel et al., eds. (1989), Greene Publishing and Wiley Interscience, New York, N.Y. The known sequence of MRP was used to query the database using the TBLAST N algorithm disclosed in Altschul et al. (1990), 215 *J. Mol. Biol.* 403–410. The query sequence is disclosed in Cole et al. (1992), 258 *Science* 1650–1654 and 260 *Science* 879. See also Seq ID No: 1 of Deeley et al. (1996), U.S. Pat. No. 5,489,519, the disclosure of which is incorporated by reference herein. The starting search parameters for TBLAST N were as follows: score=200; word length=12.

The foregoing analysis identified a novel nucleic acid sequence with detectable similarity to the query sequence. The novel sequence, disclosed herein as SEQ. ID No: 3, corresponds to a unique fragment of a hitherto unknown multidrug-resistance associated polypeptide, herein designated MRP-β. As defined herein, a "unique fragment" of a protein or nucleic acid is a peptide or oligonucleotide of sufficient length to have a sequence unique to a particular gene or polypeptide, i.e., a sequence not shared by related or unrelated genes or polypeptides. Thus, for example, a unique nucleic acid fragment typically will have at least 16 nucleotide residues, and a unique polypeptide fragment typically will have at least 6 amino acid residues. Preferably, to ensure substantially unique occurrence in a typical higher eukaryotic genome, a unique nucleic acid fragment should have at least 20 nucleotide residues, and a unique polypeptide fragment should have at least 8 amino acid residues. Unique polypeptide fragments are referred to herein as epitopes. The SEQ ID No: 3 unique fragment of MRP-β nucleic acid is 465 nucleotide residues in length and has a sequence approximately 62% identical to that of the corresponding aligned fragment of the MRP gene. In contrast, SEQ ID No: 3 lacks detectable similarity to the product of the MDR1 gene, P-glycoprotein.

A nucleic acid probe was prepared using the SEQ ID No: 3 sequence, as described in EXAMPLE 1 herein, and used for hybridization screening of an appropriate expression (cDNA) library. The screen yielded an MRP-β cDNA having the sequence set forth as SEQ ID No: 1 herein. This cloned cDNA has been designated fohd013a05m and has been deposited on even date herewith in the American Type Culture Collection under the terms of the Budapest Treaty. The sequence of ATCC DEPosit No. 94809 accordingly is incorporated herein by reference. The original SEQ ID No: 3 fragment corresponds generally to nucleotides 3635 to 4078 of the cloned SEQ ID No: 1 cDNA. The full-length MRP-β open reading frame (ORF) extends a short distance upstream (5') of the fohd013a05m MRP-β insert. The MRP-β transcript produced in human cells and/or tissue is approximately 6 kb, as visualized in the Northern blot studies described in EXAMPLES 2 and 3. The native 5' end of the cellular MRP-β gene ORF can be elucidated readily using the 5'-RACE protocol described in EXAMPLE 1.

The present invention encompasses all MRP-β nucleic acids that can be isolated or constructed by conventional molecular engineering techniques, using the information made available as a result of the present disclosure. Thus, for example, the invention encompasses nucleic acids comprising sequences complementary to all or a unique fragment of the SEQ ID No: 1 cDNA. The sequence of a "complementary" nucleic acid strand is composed of the Watson-Crick base pair partners of the nucleotide residues in a specified nucleic acid, i.e., a guanidine (G) residue corresponding to each cytosine (C) residue in the specified nucleic acid, and an adenine (A) residue corresponding to each thymidine (T) or uracil (U) residue therein. Thus, the invention encompasses RNA having a sequence complementary to SEQ ID No: 1. The present RNA can be obtained as a cell-free lysate or extract (e.g., as described in EXAMPLE 2), or can be isolated in substantially pure form using techniques described in *Current Protocols in Molecular Cloning*, Ausubel et al., eds. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y. The invention further encompasses a nucleic acid probe or primer having a nucleotide sequence complementary to a unique fragment of the MRP-β gene described herein. The probe optionally further comprises a detectable moiety, or creates a detectable complex, when hybridized to the target (MRP-β) sequence. Non-limiting examples of appropriate detectable moieties including fluorophores (e.g., fluorescein, rhodamine, Texas Red and the like), radionucleotides (e.g., $^3$H, $^{14}$C, 32p and the like), and binding-pair partners (e.g., biotin, avidin or streptavidin). The probe or primer need not be strictly complementary to the target sequence: it is only necessary that a sufficient number of probe nucleotides be capable of forming base pairs with target nucleotides to produce a stable, double-stranded nucleic acid complex under hybridization conditions.

Hybridization is the noncovalent, antiparallel bonding of complementary nucleic acid strands, in which Watson-Crick base pairing is established. To ensure specificity, hybridization should be carried out under stringent conditions, defined herein as conditions of time, temperature, probe length, probe and/or target concentration, osmotic strength, pH, detergent, carrier nucleic acid, etc. that permit no more than an occasional base-pairing mismatch within a probe/target duplex. Highly stringent conditions exclude all but about one base pair mismatch per kb of target sequence. Exemplary highly stringent conditions involve hybridization to membrane immobilized target nucleic acid at a temperature of 65c° C. in the presence of 0.5 m NaHPO$_4$, 7% SDS, 1 mM EDTA, followed by washing at 68° C. in the presence of 0.1× SSC, 0.1% SDS. *Current Protocols in Molecular Biology* (1989), Ausubel et al., eds., Greene Publishing and Wiley Interscience, New York, N.Y. In circumstances where relatively infrequent mismatches, e.g., up to about ten mismatches per kb of target, can be tolerated, moderately stringent conditions may be used. For moderate stringency, probe/target hybrids formed under the above conditions are washed at 42c° C. in the presence of 0.2× SSC, 0.1% SDS. The invention encompasses all nucleic acids that hybridize to nucleic acid, the sequence of which comprises SEQ ID No: 1 or a unique fragment thereof.

Nucleic acids that are complementary to or hybridize to all or a unique fragment of the novel MRP-β gene can be used as antisense or primer oligonucleotides. Antisense oligonucleotides disrupt gene expression and/or protein production and thereby attenuate an aberrant phenotype attributable to inappropriate expression or activation of the target gene. Lautier et al. (1996), 52 *Biochem. Pharmacol.* 967–977. As a result, the phenotype is abrogated or its penetrance is diminished (attenuated). Therapeutic intervention to attenuate a multidrug-resistance phenotype, for example, restores cellular vulnerability to cytotoxic drugs. Smyth et al. (1996), PCT Publ. WO 96/02556, teaches that antisense oligonucleotides disrupt expression of the target gene by interfering with gene transcription, transcript splicing, or translation; by triggering enzymatic destruction by RNAse H; or by destroying the target through one or more reactive moieties incorporated into the antisense compound. Preferred oligonucleotides herein have sequences sufficiently complementary to all or a unique fragment of the MRP-β gene to hybridize, under intracellular conditions, to the gene's coding or noncoding strand, or to an RNA transcript of the gene. Optionally, the oligonucleotide can be designed to hybridize to a polypeptide coding region, or to a 5' or 3' untranslated region of the gene or gene transcript, or to a gene intron or an intron/exon boundary. Typically, the present oligonucleotides are at least 9 nucleotides in length, and range from about 12 to about 40 bases in length, and are generally about 16 to 30 bases in length, with about 20 bases being considered optimal. Exemplary oligonucleotides are at least 15, 21, or 24 nucleotides in length. Specific examples of the present oligonucleotides are set forth in SEQ ID Nos: 4, 5, 6, 7 and 8. These and other exemplary oligonucleotides can be synthesized readily by conventional techniques.

While either DNA or RNA is suitable for use in primer, probe or antisense oligonucleotides, it is often desirable to include one or more modified bases, backbone sugar moieties, or backbone linking groups. Thus, Smyth et al. (1996) teaches that alkylphosphonates, phosphorothioates, phosphorodithioates, phosphate esters, alkylphosphonothioates, phosphoramidates, carbamates, carbonates, phosphate triesters, acetamidate, 2-O-methyls, and carboxymethyl esters all are suitable for use in the context of antisense oligonucleotides. Preferred modified olignoculeotides herein comprise a modified backbone structure. Peptide nucleic acid (PNA) oligonucleotides prepared according to the teachings of Perry-O'Keefe et al. (1996), 93 Proc. Nat'l. Acad. Sci. USA 14670–14675, and Egholm et al. (1993), 365 Nature 566–568, are particularly preferred herein.

In addition, the invention encompasses all MRP-β nucleic acids having sequences at least 50% identical to SEQ ID No: 1 or to the complement thereof. The determination of whether a particular sequence meets this criterion is made using the TBLAST N algorithm according to the teachings of Altschul et al. (1990), 215 J. Mol. Biol. 403–410, the teachings of which are incorporated herein by reference. Such nucleic acids encode variants, which may be naturally-occurring or biosynthetic, of the MRP-β polypeptide disclosed herein.

Similarly, the invention encompasses all nucleic acids which, by virtue of the well-known degeneracy of the genetic code, also encode the SEQ ID No: 2 polypeptide. Such degenerate variants may be naturally-occurring or may be produced through routine application of molecular engineering techniques. Current Protocols in Molecular Cloning, Ausubel et al., eds. (1989), Greene Publishing and Wiley Interscience, New York, N.Y. and in Sambrook et al. (1989), Molecular Cloning: A laboratory Manual, 2nd ed., Cold Spring Harbor Laboratory Press, Cold Spring Harbor, N.Y. Furthermore, the invention encompasses all nucleic acids encoding polypeptides having sequences that share at least 75% sequence similarity with the disclosed MRP-β polypeptide. Similarity is calculated generally according to the method of Altschul et al. (1990), 215 J. Mol. Biol. 403–410, using the TBLAST P algorithm. Moderate gaps or insertions of amino acid residues are ignored for similarity calculation purposes. Preferably, the MRP-β variants encoded by these nucleic acids function similarly to MRP-β when expressed by a host cell produced as described herein. That is, preferred MRP-β variant polypeptides are displayed on the surface of a host cell and contribute to the cell's acquisition of a multidrug-resistance phenotype. MRP-β variants thus may differ from that comprising SEQ ID No: 2 by the presence of one or more amino acid insertions, deletions, or point substitutions. Deletion variants are expected to facilitate investigation into the minimum MRP-β polypeptide structure required to support drug transport and thus multidrug-resistance phenotype. Substitution variants are expected to facilitate investigation into the mechanism and specificity of MRP-β function. Exemplary substitution variants include chimeric polypeptides in which one or more MRP-β amino acid residues are replaced by the corresponding residue in either the MRP or P-glycoprotein sequence. All nucleic acids encoding such variants are within the scope of the present invention. All oligonucleotides complementary to, or which hybridize to, the present nucleic acids are within the scope of this invention.

All of the foregoing nucleic acids of the present invention can be produced, expressed, and/or manipulated by conventional molecular engineering techniques such as the techniques set forth in Current Protocols in Molecular Cloning, Ausubel et al., eds. (1989), Greene Publishing and Wiley Interscience, New York, N.Y. and in Sambrook et al. (1989), Molecular Cloning: A Laboratory Manual, 2nd ed., Cold Spring Harbor Laboratory Press, Cold Spring Harbor, N.Y., and the teachings described and referenced in Watson et al. (1992), Recombinant DNA, 2nd ed., Scientific American Books and W. H. Freeman & Co., New York, N.Y.

Any of the foregoing nucleic acids can be inserted into an expression vector by routine molecular engineering techniques. Current Protocols in Molecular Cloning, Ausubel et al., eds. (1989), Greene Publishing and Wiley Interscience, New York, N.Y. and in Sambrook et al. (1989), Molecular Cloning: A Laboratory Manual, 2nd ed., Cold Spring Harbor Laboratory Press, Cold Spring Harbor, N.Y., and publications referenced in Watson et al. (1992), Recombinant DNA, 2nd ed., Scientific American Books and W. H. Freeman & Co., New York, N.Y. Preferred expression vectors thus encode full-length or unique fragment MRP-β polypeptides. Particularly preferred are expression vectors that, when expressed in a suitable host cell, contribute to the emergence of a multidrug-resistance phenotype therein. In other embodiments, the vector comprises DNA or RNA complementary to an antisense oligonucleotide. The present expression vectors further comprise one or more conventional expression control elements, such as an enhancer, promoter, initiation site, or termination site operatively associated with the inserted MRP-β nucleic acid. Non-limiting examples of suitable expression control elements include the cytomegalovirus immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoter of acid phosphatase, the promoters of yeast α-mating factors, and immunoglobulin enhancers and/or promoters. Optionally, the expression vector may comprise a selection marker, such as an antibiotic resistance gene. Single or multiple copies of the inserted MRP-β nucleic acid can be encoded by the vector. Preferably, for production of eukaryotic (preferably mammalian) host cells, or for therapeutic purposes, the vector is retroviral in origin or comprises one or more retroviral elements. The vector can be taken up (internalized) by cells via transfection, infection, microinjection, pinocytosis or in the course of cell division, or can be packaged, e.g., in a liposome or retroviral envelope. In this manner, the vector can be designed for selective internalization in dividing cells, transformed cells, or in cells of a tissue type susceptible to retroviral infection. Deeley et al. (1996), U.S. Pat. No. 5,489,519, the teachings of which are incorporated herein by reference, summarizes conventional techniques for the preparation of expression vectors.

The present MRP-β expression vectors are suitable for use in any conventional host cell transfection technique, e.g., as described in *Current Protocols in Molecular Cloning*, Ausubel et al., eds. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y., and in publications referenced in Watson et al. (1992), *Recombinant DNA*, 2nd ed., Scientific American Books and W. H. Freeman & Co., New York, N.Y. Thus, the present invention further provides a host cell that produces an MRP-β polypeptide or an MRP-β antisense oligonucleotide. Preferred host cells display an MRP-β polypeptide on the cell surface and/or display a multidrug-resistance phenotype. Such host cells are expected to facilitate elucidation of the types or structural classes of chemotherapeutic drugs or other substances ejected or sequestered from the intracellular milieu by MRP-β. Thus, MRP-β host cells allow rapid, in vitro evaluation of the specific characteristics of the multidrug-resistance phenotype associated with MRP-β expression or overexpression. Such cells further allow production of MRP-β polypeptides and antibodies as described below.

Cells (source cells) suitable for the production of the foregoing host cells include, but are not limited to, primary or immortalized epithelial cells such as carcinoma cells or cell lines. Additional source cells include primary or immortalized mesenchymal cells, such as sarcoma cells. Still further suitable cells include hematopoietic system cells, such as leukemia, lymphoma or lymphosarcoma cells. Mammalian or non-mammalian cells can be used, but in general, mammalian (e.g., murine, ovine, porcine, bovine or, preferably, human) cells are preferred. For certain purposes, such as the rapid phenotypic characterization of deleterious phenotypes (e.g., multidrug resistance phenotypes) conferred by MRP-β alteration, expression or overexpression, or such as the rapid screening of candidate modulators of MRP-β, non-mammalian cells such as insect cells or yeast cells, also may be used. In all circumstances, the identification of transfectants (newly produced host cells) is dependent on the use of source cells that are vulnerable to the cytotoxic effects of drugs transported by MRP-β or metabolized by the product of a selection marker gene optionally included in the vector.

Deeley et al. (1996), U.S. Pat. No. 5,489,519, Cole et al. (1994), 54 *Cancer Res.* 5902–5910, and Stride et al. (1995), 49 *Mol. Pharmacol.* 962–971, each describe the transfection of human HeLa cells with MRP to produce an MRP expressing host cell. Engel et al. (1996), U.S. Pat. No. 5,556,856, and Zelle et al. (1996), U.S. Pat. No. 5,543,423, describe the transfection of murine leukemia cells with MDR-1 to produce P-glycoprotein expressing host cells. Sarkadi et al. (1995), PCT Publ. Wo9531474 describes the transfection of murine NIH 3T3 fibroblasts and of *Spodoptera frugiperda* (insect) cells with MDR-1 to produce P-glycoprotein expressing host murine and insect cells, respectively. Ruetz et al. (1996), 271 *J. Biol. Chem.* 4154–4160, describes the transfection of *Saccharomyces cerevisiae* (yeast) with MRP and MDR-1 to produce yeast host cells. Any of the above-mentioned, available source cells can be transfected according to standard techniques with an MRP-β expression vector to produce MRP-β expressing host cells. Relevant techniques are disclosed in the above-cited references and in *Current Protocols in Molecular Cloning*, Ausubel et al., eds. (1989), Greene Publishing and Wiley Interscience, New York, N.Y. Currently, the immortalized MCF-7 human breast adenocarcinoma cell line, available from the American Type Culture Collection as ATCC No. HTB22, is a preferred source cell. An exemplary standard transfection technique suitable for use with MCF-7 is the lipofectin technique summarized in Cole et al. (1994), however, many conventional alternatives (e.g., calcium phosphate; lithium acetate; baculoviral or retroviral infection) are available and can be used with the MCF-7 or other exemplary source cell lines. After transfection, transfectants can be identified by culturing the cells in the presence of hygromycin B (as in Cole et al. (1994)) or another selection toxin, such as bisantrene or adriamycin (doxorubicin). Expression of a biologically-functional MRP-β polypeptide can be confirmed by analyzing cellular RNA for the presence of vector-derived MRP-β transcripts; by analyzing cellular protein for the presence of an epitope unique to MRP-β; by analyzing the cell surface for display of an epitope unique to MRP-β; or, by analyzing whether the cell has acquired an MRP-β associated phenotype, such as a multidrug-resistance phenotype.

The present host cells initially are expected to facilitate production of MRP-β polypeptides and structural and functional analysis thereof. The MRP-β polypeptide comprising SEQ ID No: 2 is expected to bind ATP, and to be an integral, multispanning transmembrane protein generally as described in Almquist et al. (1995), 55 *Cancer Res.* 102–110. A significant portion of the total MRP-β produced in host cells is expected to span the cells' plasma membrane, with an additional portion being present intracellularly, e.g., in the endoplasmic reticulum and/or the Golgi apparatus. Thus, MRP-β host cells are expected to display extracellular portions of the multispanning MRP-β polypeptide on the cell surface, appropriately configured to mediate the ATP-dependent sequestration or export (efflux) of a plurality of cytotoxic drugs, including drugs conventionally used as chemotherapeutic agents. These general properties are deduced from an assessment of the primary structure (sequence) of the MRP-β polypeptide. FIG. 2 sets forth an exemplary sequence alignment of the disclosed novel MRP-β polypeptide (SEQ ID No: 2), with relevant sequence of the MRP polypeptide of Deeley et al. (1996), U.S. Pat. No. 5,489,519. The alignment and identity calculations were obtained through application of the well-known Smith-Waterman algorithm for local alignment, using the PAM 120 scoring matrix described in Altschul et al. (1990), 215 *J. Mol. Biol.* 403–410, which ascertains best match between two or more sequences regardless of overall differences in sequence length. MRP-β shares approximately 42.5% amino acid sequence identity with MRP over the maximally aligned 894 amino acid residues. MRP-β accordingly is considered to be a novel member of the ABC Transporter Protein superfamily and is deemed likely to contribute to multidrug-resistance phenotypes by mediating drug transport across cellular phospholipid membranes.

The present host cells provide an appropriate purification source for obtaining useful quantities of MRP-β polypeptide. The polypeptide can be isolated in substantially pure form (i.e., essentially free of detectable levels of non-MRP-β polypeptides or other cell components) by an appropriate combination of one or more protein extraction or purification techniques such as those described in Sambrook et al. (1989), *Molecular Cloning: A Laboratory Manual,* 2nd ed., Cold Spring Harbor Laboratory Press, Cold Spring Harbor, N.Y. Alternatively, an MRP-β enriched subcellular membrane preparation can be obtained by suitable cell disruption and fractionation techniques, all of which are well-known in the art. An exemplary, adaptable protocol for obtaining an MRP enriched subcellular membrane preparation is set forth in Zamnan et al. (1994), 91 *Proc. Natl. Acad. Sci. USA* 8822–8826. Intact host cells, MRP-β enriched membrane preparations thereof, and/or isolated MRP-β protein can be used for a number of purposes, such as the production of monoclonal or polyclonal antibodies, characterization of substrates affected by MRP-β biological function, and identification of novel modulators (e.g., inhibitors) affecting MRP-β biological function.

Antibody production involves administration of one or more immunogenic doses of an MRP-β polypeptide preparation (whether isolated or incorporated in a cell membrane) to an appropriate non-human animal, such as a mouse, rat, rabbit, guinea pig, turkey, goat, sheep, pig, or horse. To enhance immunogenicity, the preparation can be emulsified with a conventional adjuvant, such as Freund's complete or incomplete adjuvant. Routine monitoring of serum immunoglobulins, using peripheral blood samples withdrawn at appropriate intervals (e.g., seven to ten days) after an initial or subsequent immunization, can be used to detect the onset and/or maturation of a humoral immune response. Detection and, optionally, quantitation, of immunoglobulins selectively reactive with an MRP-β epitope can be achieved through any conventional technique, such as ELISA, radioimmunoassay, Western blotting, or the like. Appropriate means of eliciting and monitoring production of antibodies with selective reactivity (binding) for other multidrug-resistance associated proteins are disclosed in Arceci et al. (1994), U.S. Pat. No. 5,369,009, which is incorporated herein by reference. An immunoglobulin "selectively reactive with an MRP-β epitope" has binding specificity for the recognized epitope such that an antibody/epitope complex forms under conditions generally permissive of the formation of such complexes (e.g., under conditions of time, temperature, ionic strength, pH, ionic or nonionic detergent, carrier protein, etc.). Serial dilution (titration) analysis by standard techniques is useful to estimate the avidity of antibodies in the immune serum sample for one or more epitopes unique to MRP-β. As defined herein, an "epitope unique to MRP-β" is a unique, immunogenic fragment of the full-length MRP-β polypeptide. A unique linear epitope typically ranges in size from about ten to about twenty-five amino acid residues, and frequently is about twelve to eighteen residues in length. Unique conformational epitopes also are provided herein, and comprise two or more unique fragments of the MRP-β polypeptide that, due to their juxtaposition in the folded polypeptide, form a single immunogenic epitope.

Immune serum having a high titer generally is preferred herein. Serum having a half-maximal avidity for a unique MRP-β epitope of at least about 1:1000, preferably at least about 1:10,000, can be harvested in bulk for use as a source of polyclonal antibody useful in the detection and/or quantitation of MRP-β. Polyclonal immunoglobulins can, if desired, be enriched by conventional fractionation of such serum, or can be isolated by conventional immunoadsorbent techniques, e.g., using a Protein A or Protein G chromatography resin. Immune, high titer murine or guinea pig serum alternatively is preferred herein for the production and screening of hybridomas secreting monoclonal antibodies selectively reactive with MRP-β. The present hybridomas can be produced according to well-known, standard techniques. The present monoclonal antibodies can be obtained from hybridoma culture supernatant, or from conventionally produced ascites fluid, and optionally isolated via immunoadsorbent chromatography or another suitable separation technique prior to use as agents to detect and/or quantitate MRP-β.

A preferred antibody, whether polyclonal or monoclonal, is selectively reactive with a unique MRP-β epitope that is displayed on the surface of MRP-β expressing cells, such as a host cell as provided herein. The preferred antibody accordingly can be used to detect and, if desired, quantitate MRP-β expressing cells, e.g., normal or transformed cells in a mammalian body tissue or biopsy sample thereof. Exemplary analogous methods for the use of antibodies reactive with epitopes unique to P-glycoprotein are disclosed in Arceci et al. (1994), U.S. Pat. No. 5,369,009; exemplary analogous methods for the use of antibodies reactive with epitopes unique to MRP are disclosed in Deeley et al. (1996), U.S. Pat. No. 5,489,519. Both disclosures are incorporated herein by reference. Specifically, the preferred antibody can be used to detect MRP-β expressing cells whether such cells are host cells or mammalian body tissue cells that aberrantly express MRP-β as a result of exposure to a selection toxin such as a chemotherapeutic drug. Advantageously, intact, e.g., living, cells that display a unique MRP-β epitope can be detected by standard immunohistochemical, radiometric imaging or flow cytometry techniques. The present antibody can be used to detect and/or monitor MRP-β polypeptide production in lieu of or in addition to detecting MRP-β gene expression using the novel MRP-β nucleic acids provided herein. Thus, the antibody can be used to assess whether an aberrant phenotype, such as a multidrug-resistance phenotype, in a given cell population is associated with cell surface display of MPR-α. Further, the antibody can be used to assess the natural tissue-specific production of MRP-β, and thus to assess issues likely to give rise to multidrug-resistant carcinomas or sarcomas. In addition, the present antibody can be used to monitor tumor biopsy samples to provide information relevant to selecting or revising a course of disease management, or to diagnosis, prognostication and/or staging of any disease associated with an abnormality affecting MRP-β. An exemplary disease is proliferative neoplastic disease. Furthermore, the present antibody can be used in a cell-sorting procedure or other cell isolation procedure to generate a substantially pure preparation of MRP-β expressing cells, or a cell population substantially depleted of MRP-β expressing cells. Each of the foregoing can be achieved through routine practice or modification of well-known techniques, including but not limited to the conjugation of a detectable moiety (e.g., a radionuclide, fluorophore, chromophore, binding pair member, or enzyme) to the MRP-β reactive antibody.

A hybridoma secreting an MRP-β reactive monoclonal antibody of the present invention additionally provides a suitable source of nucleic acid for the routine construction of a fusion polypeptide comprising an antigen-binding fragment derived from the MRP-β reactive antibody. The present fusion polypeptide can be prepared by routine adaptation of conventional techniques therefor in Deeley et al. (1996), U.S. Pat. No. 5,489,519 (incorporated herein by reference). The fusion polypeptide can be a truncated immunoglobulin, an immunoglobulin having a desired constant region (e.g., IgG in lieu of IgM), or a "humanized" immunoglobulin having an MRP-β reactive Fv region fused to a framework region of human origin. Additional fusion polypeptides can comprise, in addition to an MRP-β reactive antigen-binding fragment, a non-immunoglobulin polypeptide such as a cytotoxic polypeptide (e.g., diphtheria toxin, ricin) or a chemoattractant polypeptide that stimulates immune effector cells (cytotoxic T cells, natural killer cells, macrophages) to kill cells that display MRP-β. Standard techniques well-known in the art can be used to produce appropriate immunoglobulin fusion polypeptides of the present invention.

The foregoing compositions can be used for a number of purposes, including the assessment (e.g., for diagnostic purposes) of abnormalities in the structure and/or expression of a cellular MRP-β gene. Thus, for example, the invention provides a method for detecting an abornality in a cellular MRP-β gene, such as a mutation arising in germline or somatic cellular genomic DNA. Similarly, the present method provides a means for detecting chromosomal rearrangement, restriction fragment polymorphism, allelic loss or disruption of a native methylation pattern in the MRP-β gene. This method exploits the hybridization properties of an oligonucleotide probe or primer described herein. A preferred oligonucleotide is modified by the presence of a detectable label and/or a peptide nucleic acid backbone. Such oligonucleotides, which hybridize to one or more unique fragments of a cellular MRP-β gene suspected of harboring a structural (e.g., sequence) abnormality, can be used in a diagnostic protocol as disclosed in Perry-O'Keefe et al. (1996), 93 *Proc. Nat'l. Acad. Sci. USA* 14670–14675, or as disclosed in Ravnik-Glavac et al. (1994), 3 *Hum. Mol. Biol.* 801–807. Other nucleic acid-based diagnostic methods that can be exploited for purposes of assessing MRP-β gene abnormalities are as set forth in Myers et al. (1985), 230 *Science* 1242; Cotton et al. (1988), 85 *Proc. Nat'l. Acad. Sci. USA* 4397; Suleeba et al. (1992), 217 *Meth. Enzymol.* 286–295; Orita et al. (1 989), 86 *Proc. Nat'l. Acad. Sci. USA* 2766; Cotton et al. (1993), 285 *Mutat. Res.* 125–144; Hayashi (1992), 9 *Genet. Anal. Tech. Appl.* 73–79; and, Myers et al. (1985), 313 *Nature* 495. Additional methods are based on selective amplification and/or extension of MRP-β PCR primers, e.g., as described in Landegran et al. (1988), 241 *Science* 1077–1080; Nakazawa et al. (1994), 91 *Proc. Nat'l. Acad. Sci. USA* 360–364; and Abravaya et al. 91995), 23 *Nucl. Acids Res.* 675–682, and in publications referenced in Watson et al. (1992), *Recombinant DNA* 2nd ed., Scientific American Books and W. H. Freeman & Co., New York, N.Y.

Additional diagnostic and/or characterization methods using nucleic acid compositions provided herein include Northern blot, slot blot or similar methods for visualizing fluctuations, especially abnormal overproduction, in the level of cellular transcripts comprising MRP-β sequences. These methods rely on the use of MRP-β oligonucleotide probes and hybridization conditions appropriate for the formation of probe/RNA hybrids. Exemplary conditions for use with nucleic acid or modified nucleic acid probes are as set forth in Perry-O'Keefe et al. (1996), 93 *Proc. Nat'l. Acad. Sci. USA* 14670–14675; *Current Protocols in Molecular Cloning*, Ausubel et al., eds. (1989), Greene Publishing and Wiley Interscience, New York, N.Y. and Sambrook et al. (1989), *Molecular Cloning: A Laboratory Manual,* 2nd ed., Cold Spring Harbor Laboratory Press, Cold Spring Harbor, N.Y. An exemplary transcript hybridization protocol is set forth in EXAMPLE 2 herein. This example confirms the association of MRP-β expression with the occurrence of a multidrug-resistance phenotype transformed cell populations. Similar confirmation can be obtained by comparing a normal cell population with a tissue-matched transformed multidrug resistant population. Preferably, the cell populations each are derived from an exemplary mammalian body tissue, such as an epithelial tissue (e.g., mammary, respiratory tract, gastrointestinal tract, urogenital tract, paracrine, endocrine or neuroendocrine tissue). EXAMPLE 2 demonstrates that MRP-β expression is significantly elevated in multidrug-resistant derivatives of well-known cell lines, including the MCF-7 breast adenocarcinoma cell line, the HL-60 promyelocytic leukemia cell line, the A2780 ovarian carcinoma cell line, and the U937 myeloid leukemia cell line. Thus, MRP-β expression level correlates with the occurrence of multidrug-resistance rather than with derivation from a particular body tissue type.

Cellular MRP-β gene expression level similarly is expected to correlate with the maintenance or reappearance of multidrug resistance in transformed cells in situ following exposure to one or more chemotherapeutic drugs, or to a conventional chemosensitizer or "MDR reversal" agent. In other words, MRP-β gene expression activation or transcript stabilization is deemed likely to provide transformed cells with a selective advantage that is distinct from the advantage (s) derivable from P-glycoprotein or MRP expression. As a result, the monitoring of MRP-β transcript or polypeptide production, or gene expression level, or fluctuations therein, in one or more tumor biopsy samples is expected to provide information relevant to diagnosis, prognostication and/or staging of neoplastic disease in a cancer sufferer. Any suitable means for detecting MRP-β transcript or polypeptide production or stabilization, or gene expression level, can be applied for the present diagnostic purposes. Thus, gene expression can be monitored using any appropriate nucleic acid based method described above. MRP-β polypeptide production or accumulation can be monitored using an MRP-β antibody described herein. Any appropriate conventional method for visualizing selective binding of an antibody to its cognate epitope may be used. Appropriate methods are described in Sambrook et al. (1989), *Molecular Cloning: A Laboratory Manual,* 2nd ed., Cold Spring Harbor Laboratory Press, Cold Spring Harbor, N.Y.

In some embodiments, diagnosis is achieved by hybridization techniques involving the use of a modified MRP-β probe as described herein. A preferred technique involved the use of a peptide-nucleic acid probe as described in Egholm et al. (1993), 365 *Nature* 566–568, and Perry-O'Keefe et al. (1996), 93 *Proc. Natl. Acad. Sci. USA* 14670–14675. Thus, for example, the protocol of EXAMPLE 2 can be routinely adapted to allow assessment of multidrug-resistant transformed cells that have survived exposure in situ to a chemosensitizer or to an agent that interferes with P-glycoprotein or MRP expression. Further exemplary demonstrations can be produced by routinely adapting the EXAMPLE 2 protocol to the assessment of two or more biopsy samples obtained from an individual (e.g., a cancer sufferer) at different times. Preferably, a first biopsy sample corresponds to a time of diagnosis or to a time prior to or concomitant with the onset of chemotherapy. A second biopsy sample corresponds to a timepoint at which beneficial results of chemotherapy are expected to be detectable (e.g., a time sufficiently following the onset of chemotherapy for cytotoxic effects to be observed). One or more subsequent biopsy samples may correspond to further timepoints optionally correlated with fluctuations in clinical parameters (e.g., relapse, remission, a change in disease staging, or the like). Changes (fluctuations) in MRP-β gene expression, transcript stabilization, polypeptide production, and/or polypeptide stabilization are expected to correlate with, or to predict, the emergence or attenuation of a deleterious phenotype associated with MRP-β, such as a multidrug-resistance phenotype.

It will be appreciated that the causes of multidrug-resistance phenotypes vary with each individual cell type and are not wholly accounted for by expression or overexpression of P-glycoprotein, MRP or the novel MRP-β disclosed herein. Rather, additional members of the ABC Transporter Protein family may be involved, as may be one or more members of known or novel signal tranduction pathways or intracellular metabolic or growth-regulatory pathways. The present discovery of MRP-β facilitates investigation into the role(s) of such additional gene expression products in the acquisition and/or maintenance of a multidrug-resistance phenotype. Specifically, the discovery of MRP-β provides an improved method of identifying a gene, especially a hitherto unknown gene, expression of which contributes to emergence or maintenance of drug-resistant phenotype in transformed mammalian cells.

The identification method is an adaptation of the differential display technique disclosed in Liang et al. (1997), U.S. Pat. No. 5,599,672 and Pardee et al. (1993), U.S. Pat. No. 5,262,31 1. The method involves the steps of providing a transformed or normal cell population (the first population) derived from an exemplary mammalian tissue, such as a secretory epithelium (a nonlimiting example of which would be mammary epithelium), and culturing the cell population in the presence of a selection toxin, such that a drug-resistant derivative population (the second population) is produced. Mirsky et al. (1987), 47 *Cancer Res.* 2594–2598, provides an exemplary protocol for selecting a drug-resistant derivative of an immortalized human small cell lung carcinoma cell line, H69. This exemplary protocol can be adapted to use with additional cell lines, or with primary cells in culture. Thus, Halt et al. (1992), U.S. Pat. No. 5,104,858, teaches the stepwise selection of a doxorubicin-resistant derivative of the well-known MCF-7 breast adenocarcinoma cell line. Further adaptations include, e.g., the use of a selection toxin other than adriamycin. Powell et al. (1995 and 1996), U.S. Pat. Nos. 5,387,685, 5,550,149 and 5,561, 141, teaches the use of bisantrene to select for a multidrug-resistant derivative of the known human ovarian carcinoma cell line, OVCAR-3 (HTB-161). If desired, the first and second populations can be selected from well-known cell lines and/or available multidrug-resistant derivatives thereof. Sunkara (1996), U.S. Pat. No. 5,523,304, teaches the use of a multidrug-resistant human epidermoid carcinoma cell line, KBV1. Ramu et al. (1993), U.S. Pat. No. 5,190,946, teaches the use of a murine leukemia cell line (P388) and an available multidrug-resistant derivative thereof (P388/ADR). Alternatively, the populations can be selected from biopsy samples withdrawn from an individual (e.g., a cancer sufferer) before and after a clinical observation of multidrug resistance. Currently, the MCF-7 cell line and multidrug-resistant derivatives thereof are considered exemplary and are preferred for analysis of multidrug-resistance phenotypes.

Expressed nucleic acids (transcription products; RNA) are isolated separately from the first and second populations, and fractionated by electrophoretic resolution or another conventional technique as described in Liang et al. (1997), U.S. Pat. No. 5,599,672. Alternatively, the expression products of the first population are used as an adsorbent to deplete the expression products of the second population of individual transcripts that are common to both populations. Thereafter, the resolved expression products are analyzed to identify one or more gene transcripts that are preferentially expressed, underexpressed or overexpressed in the second population. Such gene transcripts accordingly are associated with the multidrug-resistance phenotype. One or more probes complementary to the novel MRP-β nucleic acids disclosed herein thus can be used as an internal control to monitor successful identification of multidrug-resistance associated gene transcripts. Of course, probes complementary to nucleic acids encoding P-glycoprotein and/or MRP can be used similarly. Multidrug-resistance associated gene transcripts that are identified in this adaptation of the Liang et al. (1996) method are subjected to routine sequencing and, if previously unknown (or unknown to be correlated with multidrug-resistance) may be cloned according to conventional molecular engineering techniques as described in *Current Protocols in Molecular Cloning*, Ausubel et al., eds. (1989), Greene Publishing and Wiley Interscience, New York, N.Y. In this manner, the MRP-β probes and/or primers described herein can be used as research tools to identify and/or produce clones of hitherto unknown genes that contribute to multidrug-resistance phenotypes, such as genes that regulate cellular expression of P-glycoprotein, MRP and/or MRP-β.

The compositions provided as a result of this invention furthermore are useful tools for the characterization of MRP-β polypeptide structure, biological function and regulation in normal mammalian cells and body tissues. The availability of information concerning the biological role of MRP-β is expected to facilitate the design, production and use of therapeutic agents to treat abnormal phenotypes, particularly disease-related phenotypes, contributed to by aberrancies in MRP-β. As part of this characterization effort, the natural expression pattern of MRP-β was surveyed in diverse mammalian body tissues. Expression products (total or poly-A(+) RNA) derived from a plurality of human body tissues were screened for hybridization with a unique MRP-β probe fragment as described in EXAMPLE 3. Transport or secretion function attributable to MRP-β was expected to affect gene expression in cells and/or tissues responsible for the secretion or excretion of cellular products or metabolites. MRP-β was observed to be expressed, at least at low (detectable baseline) levels, in substantially all body tissues. MRP-β expression similarly can be surveyed in cell types characteristic of a particular body tissue. For this more refined survey, cell types can be enriched and/or isolated from intact body tissues by convention mincing, homogenization, collagenase or trypsin digestion procedures, followed by filtration, sedimentation, adherence or panning procedures well known in the art. Alternatively, cell cultures or cell lines derived from specific body cell types may be used.

Inappropriate alteration of a cellular MRP-β gene, aberrant gene expression, transcript stabilization, or inappropriate biological function or stabilization of an MRP-β polypeptide is expected to correlate generally with tissue or cell types with a known propensity for generating transformed cells with inherent or readily acquired multidrug-resistance, especially multidrug-resistance that is refractory to treatment with known chemosensitizing agents or MDR reversal agents. MRP-β production or activity accordingly is likely to fluctuate in secretory epithelial tissues, e.g., respiratory tract, gastrointestinal tract, mammary, urogenital tract, paracrine, endocrine, and neuroendocrine tissues. Sarcomas, carcinomas, especially adenocarcinomas, originating from such tissue, particularly those originating from lung, colon, kidney, bladder, breast, ovarian, uterine, cervical, testicular, prostate or pancreatic tissue, similarly are expected to inappropriately produce MRP-β and to display or acquire multidrug-resistance phenotypes. Indeed, confirmation of such fluctuations already has been obtained, in FXAMPLE 2.

Abnormal or aberrant phenotypes, especially multidrug-resistance associated phenotypes, that are contributed to by abnormalities affecting MRP-β, can be treated using pharmaceutical or therapeutic compositions provided herein. More specifically, the invention provides therapeutic compositions, including prophylactic, palliative and remedial compositions, useful for treatment of any disease state or deleterious condition contributed to by an abnormality affecting MRP-β. A first category of such therapeutic compositions comprise an antisense oligonucleotide, or a vector encoding an antisense oligonucleotide, that hybridizes to nucleic acid corresponding to or transcribed from a cellular MRP-β gene. Stewart et al. (1996), 51 *Biochem. Pharmacol.* 461–469, and Baracchini et al. (1996), U.S. Pat. No. 5,510, 239, report successful, antisense-mediated attenuation of an MRP multidrug-resistance phenotype in cultured H69AR cells: exposure to antisense oligonucleotides significantly reduced intracellular MRP transcript and polypeptide levels. The techniques and administration methods disclosed therein can be adapted to provide antisense-mediated attenuation of an MRP-β phenotype as disclosed herein. Stewart et al. (1996) report, however, that attenuation was achieved only transiently, due to the rate of cellular production of new MRP gene transcripts and/or degradation of the antisense oligonucleotide Stewart et al. (1996) notes that, in the adriamycin selected multidrug-resistant H69AR cells, the phenotype cannot be attributed entirely to MRP expression, and for this reason counsels that antisense oligonucleotides should be used that are complementary to gene regions known to be conserved among members of the ABC Transporter Protein family. Similarly, Smyth et al. (1996), PCT Publ. WO 96/02556, reports successful, antisense oligonucleotide mediated, attenuation of a P-glycoprotein based multidrug resistance phenotype in cultured cells wherein the phenotype arises solely from P-glycoprotein production. By their nature, antisense oligonucleotides are limited to disruption of their specific target genes. Thus, the desired result of phenotypic attenuation will not be achieved where the multidrug resistance phenotype arises from (or is preserved by) expression of one or more previously unknown genes, to which the antisense oligonucleotide is unable to hybridize effectively under intracellular conditions.

This limitation is emphasized by the disclosure herein of the present novel MRP-β. However, the present disclosure provides basis for the design and construction of the present novel antisense oligonucleotides (and oligonucleotide analogs comprising one or more of the modifications mentioned in Smyth et al. (1996)) competent to hybridize, under intracellular conditions, to all or a unique portion of the MRP-β gene or a transcript thereof. The present antisense oligonucleotides can be used alone or formulated as a cocktail together with one or more of the above-mentioned antisense oligonucleotides specific to MRP or the MDR-1 gene. Antisense oligonucleotides specific for MRP-β can be produced by conventional synthetic or biosynthetic techniques, and formulated together with pharmaceutically acceptable carriers and/or excipients into antisense pharmaceutical compositions suitable for local or systemic administration to an individual, e.g., a cancer sufferer. Suitable pharmaceutical carriers and routes of administration are described in Baracchini et al. (1996), U.S. Pat. No. 5,510, 239, and Deeley et al. (1996), U.S. Pat. No. 5,489,519, the teachings of each of which are incorporated herein by reference.

The present MRP-β antisense oligonucleotides accordingiy can be used to attenuate any undesirable phenotype associated with MRP-β such as but not limited to a multidrug-resistance phenotype attributable in whole or in part to MRP-β expression or overexpression, e.g., in transformed cells in situ in mammalian body tissue. The present antisense oligonucleotides thus make possible a novel method of potentiating chemotherapy to eradicate multidrug-resistant transformed cells from the body of a mammal. The effectiveness of chemotherapy is "potentiated" (enhanced) by restoring or improving vulnerability of the transformed cells to the cytotoxic effects of a chemotherapeutic drug that otherwise would be ejected from the cell. The method involves administering the desired chemotherapeutic drug to an individual afflicted with a multidrug-resistant transformed cell population (a tumor, e.g., a carcinoma, sarcoma, leukemia, lymphoma or lymphosarcoma), and coadministering an above-described antisense pharmaceutical composition. The administration and coadministration steps can be carried out concurrently or in any order, and can be separated by a time interval sufficient to allow uptake of either compound by the transformed cells to be eradicated. For example, the present antisense pharmaceutical composition (or a cocktail composition comprising an MRP-β antisense oligonucleotide in combination with one or more other antisense oligonucleotides) can be administered to the individual sufficiently in advance of administration of the chemotherapeutic drug to allow the antisense composition to permeate the individual's tissues, especially tissue comprising the transformed cells to be eradicated; to be internalized by transformed cells; and to disrupt MRP-β gene expression and/or protein production. The time interval required can be determined by routine pharmacokinetic means, and should be expected to vary with age, weight, sex, lean tissue content, and health status of the individual, as well as with size and body compartment location of the population of multidrug-resistant transformed cells to be eradicated.

Similar parameters should be considered in selecting a route of administration of the antisense pharmaceutical composition. Thus, the composition may be administered locally or systemically, preferably by a parenteral route. The composition can be administered intravenously, intraperitoneally, retroperitoneally, intracisternally, intramuscularly, subcutaneously, topically, intraorbitally, intranasally or by inhalation, optionally in a dispersable or controlled release excipient. One or several doses of the present composition may be administered as appropriate to achieve uptake of a sufficient amount of the present antisense oligonucleotide to produce an attenuation of multidrug-resistance phenotype in the transformed cells to be eradicated by chemotherapy.

The foregoing method alternatively can be accomplished by administration of a suitable expression vector encoding the present MRP-β antisense oligonucleotide. Use of the present vector to internally produce or overproduce the present antisense oligonucleotide is expected to overcome the limitation noted in Stewart et al. (1996), namely, to ensure a continuous or renewable level of oligonucleotide mediated disruption of MRP-β expression or production. In this manner, the multidrug-resistance phenotype can be attenuated, if necessary, for a sufficient period of time for the coadministered chemotherapeutic agent to cause the death of transformed cells.

As noted above, all of the foregoing embodiments (MRP-β nucleic acids, host cells, MRP-β protein and antibodies thereto) are useful to characterize MRP-β biological function. Natural production of the MRP-β polypeptide also in untransformed mammalian body tissues likely endows the cell with active transport or secretion properties, by which a cell metabolite, secretion product, or biological response mediator is imported or, more likely, released from the producing cell. Thus, the normal physiological function of MRP-β may be the transport of one or more lipids, or substances comprising a moiety with lipid character, across the cell membrane. For example and without being limited by speculation, MRP-β may transport a bile acid or a steroid hormone or precursor thereof. Alternatively, MRP-β may mediate cellular uptake of short-chain fatty acids as an energy source. Thus, MRP-β may transport naturally- or synthetically-sourced substances, including chemotherapeutic drugs, that have salient physical or chemical properties in common with the natural transport substrate(s). The MRP-β expressing host cells provided herein thus are expected to facilitate investigation and characterization of substances, including cytotoxins, that are subject to MRP-β mediated transport.

Classical radioassay and/or metabolic radiolabelling techniques can be adapted routinely to screening known cell metabolites and/or secretion products to determine which may be a natural MRP-β transported substrate. Phospholipids, glycolipids, extracellular matrix precursors, endocrine hormones, proinflammatory steroids, bile acids, metabolites of any of the foregoing, and the like can be radiolabeled by incorporation of $^3$H, $^{35}$S, $^{14}$C or $^{32}$P according to standard techniques. Uptake, sequestration and/or efflux of radiolabeled candidate substrates can be monitored by assessing changes in radioactivity levels (e.g., by seintillation counting, auto-radiography or a similar technique) in MRP-β host cells; in culture medium conditioned by MRP-β host cells; or, as desired, in any appropriate subcellular fraction (e.g., a vesicular fraction) prepared conventionally from MRP-β host cells. Identification of one or more natural substrates for MRP-β may be relevant to the design or selection of potential MRP-β modulators as described below.

Any conventional technique for monitoring cellular susceptibility to a cytotoxin of interest, or for monitoring intracellular accumulation, sequestration or efflux thereof, can be adapted with no more than routine experimentation to characterization of the biological (e.g., transport) properties of MRP-β. Thus, the chemosensitivity testing, accumulation and efflux assays summarized in Cole et al. (1994), 54 Cancer Res. Cancer Res. 5902–5910 can be used for characterization of MRP-β export of drugs and/or toxins such as (but not limited to) doxorubicin, vincristine, colchicine, VP-16, vinblastine, verapamil, mitoxantrone, taxol, Cyclosporin A, quinidine, progesterone, tamoxifen, epirubicin, daunorubicin, MX2, and heavy metal ions such as arsenite, arsenate, antimony tartrate, antimonate, and cadmium, whether alone or in any combination thereof. Additional suitable characterization assays include the fluorescence cell sorting techniques disclosed in Krishan (1990), 33 Meth. Cell Biol. 491–500 and in Engel et al. (1996), U.S. Pat. No. 5,556,856 (both incorporated herein by reference), which capitalize on the fluorescent properties of daunorubicin. Another suitable assay is set forth in Zelle et al. (1996), U.S. Pat. No. 5,543,423 (incorporated herein by reference), and is based on assessment of cellular uptake of vital dyes following a period of exposure to a potentially exportable cytotoxin. Additional published assays are summarized in Piwnica-Worms (1995), U.S. Pat. No. 5,403,574 (incorporated herein by reference), and are based on uptake and/or efflux of fluorescent dyes, such as rhodamine. If desired, the rapid yeast cell-growth monitoring assay set forth in Ruetz et al. (1996), 271 J. Biol. Chem. 4154–4160, also can be applied.

Additional therapeutic methods for treating abnormalities or disease states associated with MRP-β, especially with the occurrence of a multidrug-resistance phenotype, are based on the identification and use of modulators, preferably inhibitors, that affect MRP-β gene activation or expression, transcript stability, polypeptide production, post-translational processing, insertion into cellular phospholipid membranes, stabilization and/or biological function, especially transport function. A candidate substance that detectably affects (products a fluctuation in) any of the foregoing MRP-β parameters is identified herein as an MRP-β modulator. Thus, for example, a candidate that interferes with host cell resistance to a cytotoxin is identified herein as a preferred inhibitory modulator (inhibitor) of MRP-β. Candidate sustances to be subjected to screening and/or identification methods described herein available or can be produced by routine adaptations of teachings set forth in Intelligent Drug Design, A Nature Supplement, 384 Nature, Suppl. to No. 6604 (1996). Additional exemplary sources of candidate MRP-β modulators are taught in Agrafiotis et al. (1995), U.S. Pat. No. 5,463,564; Zambias et al. (1996), PCT Publ. No. WO96/22529; Hogan et al. (1996), PCT Publ. No. WO96/12482; Hogan (1995), PCT Publ. Nos. WO95/32184 and WO95/18972; and, Beutel et al. (1995), PCT Publ. No. WO95/27072. Preferred candidate substances are small molecules, e.g., elements of a combinatorial chemistry or natural products library or pharmacopoeia. Currently, multidrug-resistant derivatives of the MCF-7 cell line, or MCF-7 host cells displaying a vector-derived, cell surface MRP-β polypeptide, are preferred herein for the identification of modulators of MRP-β. Any of the above-mentioned assays can be used for the present purpose, including high-throughput cell survival assays that monitor whether the present MRP-β expressing MCF-7 cells survive exposure to cytotoxin levels at which non-resistant cells normally succumb. For example, survival of MRP-β expressing host cells can be compared to survival of mock transfected MCF-7 cells at equivalent cytotoxin concentrations.

As mentioned previously herein, several inhibitors or antagonists of the known mammalian ABC Transporter Proteins, P-glycoprotein and MRP, have been disclosed. An inhibitor or antagonist that achieves complete interference with gene expression, polypeptide production and/or function effectively reverses the multidrug-resistance phenotype, restoring cellular vulnerability to the cytotoxic effects of an otherwise exported chemotherapeutic drug. An inhibitor or antagonist that achieves partial interference also can be considered beneficial clinically, in that partial interference with drug export function "attenuates" or reduces penetrance of the multidrug resistance phenotype. Upon treatment with a partial inhibitor, cellular vulnerability to cytotoxins is increased, albeit not fully restored. Such substances are commonly referred to in the art as "MDR reversal agents" or "chemosensitizing agents." Powell et al. (1996), U.S. Pat. Nos. 5,561,141 and 5,550,149; Powell et al. (1995), U.S. Pat. No. 5,387,685; Engel et al. (1996), U.S. Pat. No. 5,556,856; Zelle et al. (1996), U.S. Pat. No. 5,543,423; Sunkara (1996), U.S. Pat. No. 5,523,304; Sunkara et al. (1993), U.S. Pat. Nos. 5,190,957 and 5,182,293; Sarkadi et al. (1995), PCT Publ. WO 95/31474; Piwnica-Worms (1995), U.S. Pat. No. 5,403,574; Hait et al. (1992), U.S. Pat. No. 5,104,856. Little structural similarity has been observed between the known classes of MDR reversal agents, or between reversal agents and exported cytotoxic drugs. Thus, high through-put screening, e.g., of naturally-sourced or synthetic chemicals in a pharmacopoeia or combinatorial library, was required to identify each currently known MDR reversal agent. Furthermore, the majority of known MDR reversal agents are specific inhibitors of either P-glycoprotein or of MRP: little to no cross-inhibition has been observed. Thus, it is expected that empirical screening will be required, for the identification of one or more modulators, preferably inhibitors, of MRP-β. Exemplary identification or screening protocols are referenced herein and appear herein in EXAMPLES 4 and 5.

All modulators of MRP-β, including partial modulators, that are identified through practice of the above-described methods, or routine modifications thereof, are considered to be within the scope of the present invention. Small molecule modulators are preferred. Inhibitory modulators (inhibitors) are especially contemplated herein. For therapeutic administration purposes, a modulator of the present invention can be administered to an individual as a pharmaceutically acceptable salt or derivative. Further, the present modulator can be formulated with any pharmaceutically acceptable carrier, excipient, adjuvant or vehicle. Appropriate pharmaceutically acceptable salts, derivatives, carriers, excipients, adjuvants and vehicles are as disclosed in Zelle et al. (1996), U.S. Pat. No. 5,543,423 (which is incorporated herein by reference) or can be produced or selected by routine modifications thereof.

The present MRP-β modulator accordingly can be used to mitigate severity of, up to an including to abrogate, any phenotype associated with an abnormality affecting MRP-β. That is, the present modulator may be used to treat or palliate any disease or condition affecting the health status of an individual, such as a human, that arises from the MRP-β abnormality. The modulator also may be administered prophylactically, to avert or delay the onset of a deleterious phenotype associated with MRP-β dysfunction. In particular, the present MRP-β modulator is useful to attenuate a multidrug-resistance phenotype attributable in whole or in part to MRP-β gene abnormality, gene expression, transcript stabilization, or polypeptide production, processing, stability or biological function, e.g., in transformed cells in situ in mammalian body tissue. Preferred inhibitory modulators make possible novel methods, for example, of potentiating chemotherapy to eradicate multidrug-resistant transformed cells from the body of a mammal. As with the antisense pharmaceutical composition method discussed herein, the effectiveness of chemotherapy is enhanced by restoring or improving vulnerability of the transformed cells to the cytotoxic effects of a chemotherapeutic drug that otherwise would be ejected from the cell. The present, modulator-based method involves administering the modulator alone or as an adjuvant to the desired chemotherapeutic drug, to an individual afflicted with a multidrug-resistant tumor, e.g., a carcinoma, sarcoma, leukemia, lymphoma or lymphosarcoma. The chemotherapeutic drug and MRP-β modulator may be administered concurrently or in any order, and can be separated by a time interval sufficient to allow uptake of either compound by the transformed cells to be eradicated. If desired, the present modulator can be administered alone or in a cocktail, combined with one or more known MDR reversal agents (e.g., agents that affect MRP or P-glycoprotein).

Preferably, the modulator is administered to the individual sufficiently in advance of administration of the chemotherapeutic drug to allow the modulator to permeate the individual's tissues, especially tissue comprising the transformed cells to be eradicated; to be internalized by transformed cells; and to impair MRP-β mediated cytotoxin sequestration or efflux. The time interval required can be determined by routine pharmacokinetic means, and should be expected to vary with age, weight, sex, lean tissue content, and health status of the individual, as well as with size and body compartment location of the population of multidrug-resistant transformed cells to be eradicated. Similar parameters should be considered in selecting a route of administration of the modulator. Thus, the modulator may be administered locally or systemically, preferably by a parenteral route. It can be administered intravenously, intraperitoneally, retroperitoneally, intracisternally, intramuscularly, subcutaneously, topically, intraorbitally, intranasally or by inhalation, optionally in a dispersable or controlled release excipient. One or several doses may be administered as appropriate to achieve uptake of a sufficient amount of the present modulator to produce an attenuation of multidrug-resistance phenotype in the transformed cells to be eradicated by chemotherapy. As a result of therapeutic intervention with an MRP-β modulator (preferably, an inhibitory modulator), penetrance of an abnormal or deleterious phenotype (generally, but not limited to, a multidrug resistance phenotype) is attentuated, even abrogated, in the treated individual. The overall dosage and administration protocol for treatment with the present modulator may be designed and optimized by the clinical practitioner through the application of routine clinical skill.

Practice of the invention will be still more fully understood from the following EXAMPLES, which are presented solely to illustrate principles and operation of the invention, and should not be construed as limiting scope of the invention in any way.

EXAMPLE 1

Isolation And Cloning Of Full-Length MRP-β cDNA.

A unique fragment (SEQ ID No: 3) of the novel MRP-β gene was identified by computer-assisted screening of a nucleic acid database corresponding to a human endothelial cell expression library. The library was prepared using cellular RNA transcripts produced in human microvascular endothelial cells (HUMVEC) isolated from breast tissue and maintained in primary culture in the presence of a commercially available extracellular matrix composition (Matrigel), and in the presence of appropriate growth and differentiation factors (e.g., vascular endothelial cell growth factor (VEGF)). These conditions had previously been shown to preserve cell viability and substantially differentiated phenotype in vitro.

A nucleic acid probe corresponding to the SEQ ID No: 3 unique fragment was prepared by conventional techniques. This probe was used for hybridization screening of the HUMVEC expression library for the presence of MRP-β cDNAs. This procedure yielded an MRP-β cDNA (FIG. 1 and SEQ ID No: 1), 4.78 kb (kilobases) in length. The clone comprising this cDNA insert has been designated fohd013a05m and deposited with the American Type Culture Collection. It has been accorded ATCC Deposit No. 94809. The open reading frame (ORF) of the SEQ ID No: 1 cDNA encodes an MRP-β polypeptide (SEQ ID No: 2) 1454 amino acid residues in length and in addition, includes a 0.42 kb 3' untranslated region.

Based upon the results of the Northern blot MRP-β gene expression studies summarized below in EXAMPLES 2 and 3, it is anticipated that the full-length ORF of the MRP-β gene extends approximately 1 kb upstream (5') from the fohd013a05m insert. A single, full-length MRP-β cDNA clone can be obtained easily through use of the Marathon RACE protocol and reagents available commercially through Clonetech Laboratories, Inc. RACE, or rapid amplification of cDNA ends, is useful to isolate a PCR fragment comprising the native 3' or 5' end of a cDNA open reading frame, and involves use of one or more gene-specific sense (for 3' RACE) or antisense (for 5' RACE) oligonucleotide primers. The RACE protocol is generally as described in Siebert et al. (1995), 23 Nucl. Acids Res. 1087–1088, and in the Clonetech, Inc. User Manual for Marathon-Ready cDNA (1996), the teachings of which are incorporated herein by reference. The RACE reagents include the Advantage KlenTaq Polymerase mix, 10× PCR reaction buffer, 50× dNTP mix and Tricine-EDTA buffer commercially available from Clonetech, Inc. The protocol is practiced with 0.5 mL PCR reaction tubes and a thermal cycling device such as the DNA Thermal Cycler 480 available from Perkin-Elmer Corporation.

A plurality of nested, MRP-β specific primers (antisense oligonucleotides, SEQ ID Nos: 4 to 8) each 24 bp (basepairs) in length, were prepared for use in a 5'-RACE protocol to amplify a PCR product comprising the 5' end of the MRP-β open reading frame in a HUMVEC Marathon-Ready cDNA preparation. Thermal cycling was carried out according to the manufacture's recommended Program 1 (a 94° C. hot start followed by 5 cycles at 94° C. to 72° C., then 5 cycles at 94° C. to 70° C., then 20–25 cycles at 94° C. to 68° C.). Standard electrophoretic resolution of the final PCR product confirmed the presence of a plurality of MRP-β cDNA fragments, the largest of which migrated at about 1 kb. This fragment is expected to include the native 5' end of MRP-β gene OR7. Confirmation that additional MRP-β gene sequence has been obtained can be produced by routine Southern blot analysis or by subcloning and sequencing.

The present 1 kb 5'-RACE product also is useful to produce a full-length MRP-β cDNA by long-distance PCR (generally as described in Barnes (1994), 91 Proc. Natl. Acad. Sci. USA 2216–2220, and Cheng et al. (1994), 91 Proc. Natl. Acad. Sci. USA 5695–5699) or by subcloning according to established techniques. The long-distance PCR technique involves the use of oligonucleotides corresponding to the native 5' and 3' ends of the MRP-β gene OPR in a hot start cycling program commencing at 94° C., followed by 25 cycles at 94° C. to 68° C. Electrophoretic resolution of the amplified long-distance PCR product is expected to yield a single cDNA of approximately 6 kb, encoding a full-length MRP-β polypeptide. The alternative subcloning technique capitalizes on the presence, if any, of overlapping sequence between the 5'-RACE product and the fohd013a05m cDNA insert. Exploitation of a restriction site, if present in the overlapping region, allows joinder of overlapping partial cDNAs by T4 ligase to produce a single cDNA corresponding to expressed cellular MRP-β.

EXAMPLE 2

Correlation Of MRP-β Expression Level With Multidrug-Resistance Phenotype.

Involvement of the present novel MRP-β gene in the acquisition or maintenance of a multidrug-resistance phenotype has been confirmed by comparing the level of MRP-β gene expression in immortalized, transformed cells (wild-type or parent cells) that have not acquired the property of multidrug-resistance with the level in a multidrug-resistant derivative of the parent cell population. One set of exemplary parent and multidrug-resistant derivative cell lines are described in Mirsky et al. (1987), 47 Cancer Res. 2594–2598 (parent and multidrug-resistant (MDR) derivative of the H69 human small cell lung carcinoma line). Additional exemplary parent and multidrug-resistant derivative lines are described in Slapak et al. (1994), 84 Blood 3113–3121 (parent and MDR derivative of the U937 human myeloid leukemia line); Batist et al. (1986), 261 J. Biol. Chem. 15544–15549 (parent and MDR derivative of the MCF-7 human breast adenocarcimoma line); March et al. (1986), 46 Cancer Res. 4053–4057 (parent and MDR derivative of the HL-60 human promyelocytic leukemia line); and, Hamilton et al. (1984), 11 Sem. Oncol. 285–298 (parent and MDR derivative of the A2780 human ovarian carcinoma line). Each of the foregoing references is incorporated herein by reference. To demonstrate correlation between MRP-β gene expression and multidrug-resistance phenotype, parental (wild-type) and adriamycin-selected multidrug resistant MCF-7 cells were cultured to confluency under standard cell culture conditions and treated to release expressed nucleic acid transcripts, which were subjected to Northern blot analysis.

Preparation of cellular RNA. Expressed nucleic acids were isolated from the exemplary parental and resistant MCF-7 cells using components of the Qiagen, Inc. RNeasy Total RNA kit, generally as in the Qiagen, Inc. RNeasy Handbook (1995). Kit components include spin columns, collection tubes, lysis buffer, wash buffer and RNAse free water. Expressed nucleic acid extracts were prepared by suspending cells in lysis buffer supplemented with 2-mercaptoethanol and passage of the resulting mixture through a Qiagen, Inc. Qiashredder homogenization column. RNA was purified from the resulting lysate using a Qiagen, Inc. RNeasy column supplied with the kit. The lysate was loaded onto the RNeasy colum, washed and RNA was eluted generally as described in the RNeasy Handbook.

Electrophoretic Resolution of Expressed RNAs. Agarose-formaldehyde slab gels (1.0–2.5% agarose) were prepared and cast according to standard techniques. RNA samples (10–30 μg total RNA or 1–3 μg PolyA(+) RNA) were combined with denaturing bromophenol blue sample buffer, loaded onto the gel and subjected to electrophoresis by passage of 100 volts through the gel chamber for about 3 hours or until the bromophenol blue dye front had migrated about 10 cm into the gel. A photograph of the resolved gel was obtained prior to transfer of resolved RNAs to nylon.

Replica Transfer of Resolved RNAs to Nylon. The gel comprising resolved cellular MRP-β transcript was prepared for transfer by soaking in 0.05 N NaOH, 0.15 M NaCl for 20–30 minutes, followed by neutralization in 0.1 M Tris pH 7.5, 0.15 M NaCl for 30 minutes. RNA contents of the neutralized gel were then transferred to a nylon membrane using a Posiblot apparatus (Stratagene, Inc.). Transfer was allowed to proceed for 1 hour, following which the transferred, resolved RNAs were crosslinked to the membrane using UV light generated by a Stratalinker apparatus (Stratagene, Inc.). The location of resolved RNAs on the membrane was visualized by staining with methylene blue. The positions of the RNA ladder, 18S, and 28S ribosomal RNAs were marked on a photograph taken of the stained membrane, which was then destained according to standard procedure.

Preparation of detectable labeled MRP-β Probe. A unique fragment (e.g., SEQ ID No: 3) of the MRP-β cDNA was used for the preparation of a radiolabeled hybridization probe for visualizing the electrophoretically resolved, full-length MRP-β transcript expressed in parent (wild-type) and MDR MCF-7 cells. The probe was prepared using the Stratagene, Inc. Prime It-RmT Primer Labeling Kit, generally according to the protocol supplied by the manufacturer (see also Feinberg et al. (1984) 137 *Anal. Biochem.* 266–267 and Feinberg et al. (1983), 132 *Anal. Biochem.* 6–13). Kit components include control DNA, Magenta thermostable DNA polymerase, stop mix, and dehydrated single-use reaction mixtures comprising random primers, nucleotides, buffer and cofactors required by the polymerase. To prepare the probe, 50 ng MRP-β DNA (e.g., cDNA insert comprising SEQ ID No: 3) in aqueous solution was added to a kit single-use reaction mixture and boiled to ensure denaturation. To obtain incorporation of at least $10^6$ cpm/μL, 5 μL [α-$^{32}$P]dCTP (6000 Ci/mmol) was added to the mixture, followed by 3 μL Magenta polymerase (4U/uL). Probe synthesis was conducted at 37° C. for 10 minutes, then stopped by the addition of 2 μL stop mix. To reduce background, the labeled probe was purified using a chromaspin TE-10 column prior to use for hybridization.

Hybridization. Prior to contact with the radiolabeled probe, the nylon membrane comprising crosslinked, electrophoretically resolved MCF-7 cellular transcripts was pre-hybridized for 20 minutes at 65° C. in 10 mL Rapid-hyb solution available from Amersham, Inc. The prepared probe was boiled for 5 minutes to ensure denaturation, and added to an additional 10 mL Rapid-Hyb solution. The prehybridization solution was exchanged for probe solution, and the probe was allowed to hybridize to membrane-bound transcripts for 2 hours at 65° C. Excess, unhybridized probe was removed by washing the membrane in 2× SSC, 0.1% SDS for 20 minutes, either at room temperature or at 42° C. Thereafter, the membrane was washed in 0.1× SSC, 0.1% SDS for 20 min. at 65° C. The 65° C. wash step was repeated if necessary to obtain a satisfactory signal-to-background ratio as assessed by geiger counter. Results were visualized by exposure to X-ray film according to standard procedures. Thereafter, MRP-β probe was stripped by addition of a boiling solution of 0.5% (w/v) SDS (0.1× SSC, 0.1% SDS also can be used as a stripping solution). Significance of the MRP-β results were verified by rehybridization of the membrane with a probe specific for the transcript of a conventionally used housekeeping or structural gene (e.g., Ef-TU or actin).

Results. A single 6 kb transcript was visualized by the MRP-β probe in both wild-type and MDR MCF-7 cellular RNA. A significantly elevated level of the MRP-β transcript was observed in the MDR derivative cell line, which is reported in Batist et al. (1986) to be 192-fold more resistant to adriamycin than the parental (wild-type) MCF-7 human breast adenocarcinoma cell line. Consistent results showing elevated levels of MRP-β gene expression were observed in comparison studies of parental and MDR derivative cell lines established from human ovarian carcinoma (A2780; Hamilton et al. (1984)) and human leukemias (HL-60; March et al. (1986), and U937; Slapak et al. (1994)). Thus, MRP-β gene expression level correlates with the acquisition of a multidrug-resistance phenotype, rather than with the body tissue type in which a particular tumor arises.

EXAMPLE 3

Expression Of MRP-β In Mammalian Body Tissues.

As noted above, a clearly detectable baseline level of MRP-β gene expression was observed even in wild-type tumor cell lines. To establish whether this baseline expression correlates with tumorigenesis, the above-described radiolabeled MRP-β probe was hybridized to commercially available human Multiple tissue Northern (MTN) blots (Clontech, Inc.), generally according to the manufacturer's directions and the procedure described above in EXAMPLE 2. Tissues from which polyA(+)RNA was analyzed included heart, brain, placenta, lung, liver, skeletal muscle, kidney, pancreas, spleen, thymus, prostate, testis, ovary, small intestine, colon (mucosal lining) and peripheral blood leukocyte.

Results. Clearly detectable baseline expression of a 6 kb MRP-β transcript was observed in substantially all normal human body tissues surveyed, with the highest expression level being observed in heart tissue. The survey samples represent expressed RNAs isolated from lysates of whole tissue, rather than from specific cell types characteristic of one or more body tissues. Taken together with the isolation of MRP-β cDNAs from a HUMVEC expression library (described in EXAMPLE 1), the present MTN survey data is consistent with substantially ubiquitous baseline expression of MRP-β in vasculature or microvasculature.

EXAMPLE 4

Confirmation That MRP-β Expression Is Sufficient To Confer A Survival Advantage On Cells Exposed To A Cytotoxic Agent.

Host cells stably transfected with an MRP-β expression vector as described herein are expected to gain a significant survival advantage, relative to source (untransfected) or control (antisense transfected) cells. To establish this survival advantage, triplicate cultures of MRP-β host cells, control cells and source cells (e.g., MCF-7 human breast adenocarcinoma cells) are generated in 24-well cell culture plates. Once the cultures have attained at least 80% confluency, lethal or sub-lethal amounts of a cytotoxin (e.g., adriamycin, bisantrene) are added to each well. After a sufficient period of time for cytotoxic effects to be manifested (e.g., 16–24 hours in culture), culture media comprising the cytotoxic drug are aspirated or otherwise removed, and cells are stained with a vital dye such as Trypan blue. Which commercially available vital dye is used in this procedure is a matter of choice; thus, sulforodoamine B (see Powell et al. (1990), U.S. Pat. No. 5,550,149) could be used in lieu of Trypan blue. The number of cells that remain viable (e.g., capable of excluding the dye) are counted using a hemocytometer, flow cytometer or other appropriate device.

Expected Results. MRP-β expressing host cells are expected to acquire the capability of surviving exposure to otherwise lethal amounts of a cytotoxin, such as adriamycin or bisantrene. Analysis of the differential between toxin levels that are lethal to source or control cells, and that which is lethal to MRP-β host cells, is expected to provide a predictive index of the recalcitrance of MRP-β expressing transformed cells in situ to chemotherapy. Repetition of this cytotoxicity assay with additional toxins (e.g., environmentally or occupationally derived toxins, metabolites or chemotherapeutic drugs) is expected to elucidate the nature of substances exportable or sequestrable by MRP-β and to uncover specific differences between the characteristics of substrates transported by MRP-β and those transported by known ATP Transporter Protein superfamily members such as P-glycoprotein and/or MRP.

Screening for a modulator of MRP-β. The present cytotoxicity assay can be adapted routinely to provide a rapid assay for screening candidate modulators of MRP-β. In this adaptation, host cell cultures are incubated in the presence of a toxin to which MRP-β expression confers a survival advantage. The level of toxin exposure is sub-lethal to host cells but lethal to source cells or control cells. Candidate MRP-β modulators (e.g., inhibitors) are added to the cell cultures, which are incubated for a sufficiently further period of time for cytotoxicity to be manifested (e.g., 16–24 hours). A candidate that attenuates or abrogates the host cells' survival advantage is identified as an MRP-β inhibitor. Guidelines for this adaptation of the present cytotoxicity assay may be found in Powell et al. (1996), U.S. Pat. No. 5,550,149. Candidate MRP-β modulators may be selected from any appropriate source, such as a pharmacopeia of natural or synthetic substances, combinatorial chemistry library, phage display epitope library, or the like. Appropriate sources are available or can be produced by routine adaptations of teachings set forth in *Intelligent Drug Design, A Nature Supplement*, 384 *Nature*, Suppl. to No. 6604 (1996). Additional exemplary sources of candidate MRP-β modulators are taught in Agrafiotis et al. (1995), U.S. Pat. No. 5,463,564; Zambias et al. (1996), PCT Publ. No. WO96/22529; Hogan et al. (1996), PCT Publ. No. WO96/12482; Hogan (1995), PCT Publ. Nos. WO95/32184 and WO95/18972; and, Beutel et al. (1995), PCT Publ. No. WO95/27072.

EXAMPLE 5

Assessment of MRP-β Mediated Drug Efflux.

Without being limited by speculation, it is likely that MRP-β confers the above-described survival advantage by mediating sequestration or efflux of one or more cytotoxins. That is, it is likely that MRP-β is a member of the ABC Transporter Protein superfamily that carries out an export function. However, routine empirical testing is required to confirm whether MRP-β exports one or more toxic substances, or imports one or more nutrients or energy sources, such as sugars or fatty acids of dietary or other metabolic origin. A number of conventional protocols can be practiced, with such routine modifications as may be deemed appropriate by the practitioner, to establish whether MRP-β mediates toxin export. A presently preferred technique capitalizes on the fluorescent properties of anthracycline toxins (including adriamycin (doxorubicin) and daunamycin), such that toxin accumulation and/or efflux from MRP-β expressing host cells can be monitored by fluorescence histochemistry or, preferably, by fluorescence-activated flow cytometry An example of this technique is described in Krishan (1990), 33 *Meth. Cell Biol.* 491–500, incorporated herein by reference.

Fluorescent labeling. Viable MRP-β host cells (at least 10,000) are suspended in culture medium in the sampling cuvette of a flow cytometer, such as the EPICS 753 apparatus (Coulter Electronics, Inc.) equipped with an argon laser for fluorophore excitation at 488 nm, and a photomultiplier (e.g., MDADS II data acquisition apparatus) for detection of 530 nm emissions. The cuvette is maintained at 37° C., and adriamycin or daunomycin are added to a final concentration of 1–3 $\mu$M prior to cell sorting. Two-parameter histograms are generated based on cellular fluorescence and incubation time (typically 30 to 60 minutes) in the presence of the fluorescent toxin.

Expected results. MRP-β host cells are expected to internalize and/or retain significantly lower levels of adriamycin or daunomycin than source cells or control cells.

Screening for a modulator of MRP-β. The above drug efflux assay can be adapted routinely to provide a rapid assay for screening candidate modulators of MRP-β. In this adaptation, a candidate MRP-β modulator is added to the cuvette during the fluorophore uptake incubation. A candidate that attenuates or abrogates the host cells' capacity for fluorophore efflux is identified as an MRP-β inhibitor. Guidelines for this adaptation may be found in Krishan (1990), 33 *Meth. Cell Biol.* 491–500). Candidate MRP-β modulators may be selected from any appropriate source, such as the sources mentioned in EXAMPLE 4.

Equivalents

The invention may be embodied in other specific forms without departing from the spirit or essential characteristics thereof. For example, the invention may be embodied in one or more variants, e.g., deletion, addition or substitution variants, of the nucleic acid and/or protein sequences disclosed herein, such as may be produced. routinely by mutagenesis or other conventional molecular engineering and biosynthetic production techniques. Specifically, the invention may be embodied in any variant, whether biosynthetically produced or isolated from a natural source, the expression or overexpression of which endows a mammalian cell with a multidrug-resistance phenotype. More specifically, the invention may be embodied in a variant which, when expressed or overexpressed, endows a mammalian cell with resistance to the cytotoxic effects of MRP-β transportable drugs. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 4781 base pairs
      (B) TYPE: nucleic acid
      (C) STRANDEDNESS: single
      (D) TOPOLOGY: linear 5,994,130

39

-continued (ix) FEATURE:
    (A) NAME/KEY: CDS
    (B) LOCATION: 2..4360

(xi) SEQUENCE DESCRIPTION: SEQ ID NO:1:

```
T GAT GTG AAA CTA ACA GTC TGT GAG CCC TGG AAC CTC CAC TCA GAG        46
  Asp Val Lys Leu Thr Val Cys Glu Pro Trp Asn Leu His Ser Glu
  1               5                   10                  15

AAG ATG AAG GAT ATC GAC ATA GGA AAA GAG TAT ATC ATC CCC AGT CCT      94
Lys Met Lys Asp Ile Asp Ile Gly Lys Glu Tyr Ile Ile Pro Ser Pro
                20                  25                  30

GGG TAT AGA AGT GTG AGG GAG AGA ACC AGC ACT TCT GGG ACG CAC AGA     142
Gly Tyr Arg Ser Val Arg Glu Arg Thr Ser Thr Ser Gly Thr His Arg
            35                  40                  45

GAC CGT GAA GAT TCC AAG TTC AGG AGA ACT CGA CCG TTG GAA TGC CAA     190
Asp Arg Glu Asp Ser Lys Phe Arg Arg Thr Arg Pro Leu Glu Cys Gln
        50                  55                  60

GAT GCC TTG GAA ACA GCA GCC CGA GCC GAG GGC CTC TCT CTT GAT GCC     238
Asp Ala Leu Glu Thr Ala Ala Arg Ala Glu Gly Leu Ser Leu Asp Ala
    65                  70                  75

TCC ATG CAT TCT CAG CTC AGA ATC CTG GAT GAG GAG CAT CCC AAG GGA     286
Ser Met His Ser Gln Leu Arg Ile Leu Asp Glu Glu His Pro Lys Gly
80                  85                  90                  95

AAG TAC CAT CAT GGC TTG AGT GCT CTG AAG CCC ATC CGG ACT ACT TCC     334
Lys Tyr His His Gly Leu Ser Ala Leu Lys Pro Ile Arg Thr Thr Ser
                100                 105                 110

AAA CAC CAG CAC CCA GTG GAC AAT GCT GGG CTT TTT TCC TGT ATG ACT     382
Lys His Gln His Pro Val Asp Asn Ala Gly Leu Phe Ser Cys Met Thr
            115                 120                 125

TTT TCG TGG CTT TCT TCT CTG GCC CGT GTG GCC CAC AAG AAG GGG GAG     430
Phe Ser Trp Leu Ser Ser Leu Ala Arg Val Ala His Lys Lys Gly Glu
        130                 135                 140

CTC TCA ATG GAA GAC GTG TGG TCT CTG TCC AAG CAC GAG TCT TCT GAC     478
Leu Ser Met Glu Asp Val Trp Ser Leu Ser Lys His Glu Ser Ser Asp
    145                 150                 155

GTG AAC TGC AGA AGA CTA GAG AGA CTG TGG CAA GAA GAG CTG AAT GAA     526
Val Asn Cys Arg Arg Leu Glu Arg Leu Trp Gln Glu Glu Leu Asn Glu
160                 165                 170                 175

GTT GGG CCA GAC GCT GCT TCC CTG CGA AGG GTT GTG TGG ATC TTC TGC     574
Val Gly Pro Asp Ala Ala Ser Leu Arg Arg Val Val Trp Ile Phe Cys
                180                 185                 190

CGC ACC AGG CTC ATC CTG TCC ATC GTG TGC CTG ATG ATC ACG CAG CTG     622
Arg Thr Arg Leu Ile Leu Ser Ile Val Cys Leu Met Ile Thr Gln Leu
            195                 200                 205

GCT GGC TTC AGT GGA CCA GCC TTC ATG GTG AAA CAC CTC TTG GAG TAT     670
Ala Gly Phe Ser Gly Pro Ala Phe Met Val Lys His Leu Leu Glu Tyr
        210                 215                 220

ACC CAG GCA ACA GAG TCT AAC CTG CAG TAC AGC TTG TTG TTA GTG CTG     718
Thr Gln Ala Thr Glu Ser Asn Leu Gln Tyr Ser Leu Leu Leu Val Leu
    225                 230                 235

GGC CTC CTC CTG ACG GAA ATC GTG CGG TCT TGG TCG CTT GCA CTG ACT     766
Gly Leu Leu Leu Thr Glu Ile Val Arg Ser Trp Ser Leu Ala Leu Thr
240                 245                 250                 255

TGG GCA TTG AAT TAC CGA ACC GGT GTC CGC TTG CGG GGG GCC ATC CTA     814
Trp Ala Leu Asn Tyr Arg Thr Gly Val Arg Leu Arg Gly Ala Ile Leu
                260                 265                 270

ACC ATG GCA TTT AAG AAG ATC CTT AAG TTA AAG AAC ATT AAA GAG AAA     862
Thr Met Ala Phe Lys Lys Ile Leu Lys Leu Lys Asn Ile Lys Glu Lys
            275                 280                 285

TCC CTG GGT GAG CTC ATC AAC ATT TGC TCC AAC GAT GGG CAG AGA ATG     910
Ser Leu Gly Glu Leu Ile Asn Ile Cys Ser Asn Asp Gly Gln Arg Met
```

```
                 290                     295                     300
TTT GAG GCA GCA GCC GTT GGC AGC CTG CTG GCT GGA GGA CCC GTT GTT    958
Phe Glu Ala Ala Ala Val Gly Ser Leu Leu Ala Gly Gly Pro Val Val
    305                     310                     315

GCC ATC TTA GGC ATG ATT TAT AAT GTA ATT ATT CTG GGA CCA ACA GGC   1006
Ala Ile Leu Gly Met Ile Tyr Asn Val Ile Ile Leu Gly Pro Thr Gly
320                     325                     330                 335

TTC CTG GGA TCA GCT GTT TTT ATC CTC TTT TAC CCA GCA ATG ATG TTT   1054
Phe Leu Gly Ser Ala Val Phe Ile Leu Phe Tyr Pro Ala Met Met Phe
                340                     345                     350

GCA TCA CGG CTC ACA GCA TAT TTC AGG AGA AAA TGC GTG GCC GCC ACG   1102
Ala Ser Arg Leu Thr Ala Tyr Phe Arg Arg Lys Cys Val Ala Ala Thr
            355                     360                     365

GAT GAA CGT GTC CAG AAG ATG AAT GAA GTT CTT ACT TAC ATT AAA TTT   1150
Asp Glu Arg Val Gln Lys Met Asn Glu Val Leu Thr Tyr Ile Lys Phe
        370                     375                     380

ATC AAA ATG TAT GCC TGG GTC AAA GCA TTT TCT CAG AGT GTT CAG AAA   1198
Ile Lys Met Tyr Ala Trp Val Lys Ala Phe Ser Gln Ser Val Gln Lys
385                     390                     395

ATC CGC GAG GAG GAG CGT CGG ATA TTG GAA AAA GCC GGG TAC TTC CAG   1246
Ile Arg Glu Glu Glu Arg Arg Ile Leu Glu Lys Ala Gly Tyr Phe Gln
400                     405                     410                 415

AGC ATC ACT GTG GGT GTG GCT CCC ATT GTG GTG GTG ATT GCC AGC GTG   1294
Ser Ile Thr Val Gly Val Ala Pro Ile Val Val Val Ile Ala Ser Val
                420                     425                     430

GTG ACC TTC TCT GTT CAT ATG ACC CTG GGC TTC GAT CTG ACA GCA GCA   1342
Val Thr Phe Ser Val His Met Thr Leu Gly Phe Asp Leu Thr Ala Ala
            435                     440                     445

CAG GCT TTC ACA GTG GTG ACA GTC TTC AAT TCC ATG ACT TTT GCT TTG   1390
Gln Ala Phe Thr Val Val Thr Val Phe Asn Ser Met Thr Phe Ala Leu
        450                     455                     460

AAA GTA ACA CCG TTT TCA GTA AAG TCC CTC TCA GAA GCC TCA GTG GCT   1438
Lys Val Thr Pro Phe Ser Val Lys Ser Leu Ser Glu Ala Ser Val Ala
465                     470                     475

GTT GAC AGA TTT AAG AGT TTG TTT CTA ATG GAA GAG GTT CAC ATG ATA   1486
Val Asp Arg Phe Lys Ser Leu Phe Leu Met Glu Glu Val His Met Ile
480                     485                     490                 495

AAG AAC AAA CCA GCC AGT CCT CAC ATC AAG ATA GAG ATG AAA AAT GCC   1534
Lys Asn Lys Pro Ala Ser Pro His Ile Lys Ile Glu Met Lys Asn Ala
                500                     505                     510

ACC TTG GCA TGG GAC TCC TCC CAC TCC AGT ATC CAG AAC TCG CCC AAG   1582
Thr Leu Ala Trp Asp Ser Ser His Ser Ser Ile Gln Asn Ser Pro Lys
            515                     520                     525

CTG ACC CCC AAA ATG AAA AAA GAC AAG AGG GCT TCC AGG GGC AAG AAA   1630
Leu Thr Pro Lys Met Lys Lys Asp Lys Arg Ala Ser Arg Gly Lys Lys
        530                     535                     540

GAG AAG GTG AGG CAG CTG CAG CGC ACT GAG CAT CAG GCG GTG CTG GCA   1678
Glu Lys Val Arg Gln Leu Gln Arg Thr Glu His Gln Ala Val Leu Ala
545                     550                     555

GAG CAG AAA GGC CAC CTC CTC CTG GAC AGT GAC GAG CGG CCC AGT CCC   1726
Glu Gln Lys Gly His Leu Leu Leu Asp Ser Asp Glu Arg Pro Ser Pro
560                     565                     570                 575

GAA GAG GAA GAA GGC AAG CAC ATC CAC CTG GGC CAC CTG CGC TTA CAG   1774
Glu Glu Glu Glu Gly Lys His Ile His Leu Gly His Leu Arg Leu Gln
                580                     585                     590

AGG ACA CTG CAC AGC ATC GAT CTG GAG ATC CAA GAG GGT AAA CTG GTT   1822
Arg Thr Leu His Ser Ile Asp Leu Glu Ile Gln Glu Gly Lys Leu Val
            595                     600                     605

GGA ATC TGC GGC AGT GTG GGA AGT GGA AAA ACC TCT CTC ATT TCA GCC   1870
Gly Ile Cys Gly Ser Val Gly Ser Gly Lys Thr Ser Leu Ile Ser Ala
```

-continued

|     |     |     |     |     |     |     |     |     |     |     |     |     |      |
| --- | --- | --- | --- | --- | --- | --- | --- | --- | --- | --- | --- | --- | ---- |
|     |     | 610 |     |     |     | 615 |     |     |     | 620 |     |     |      |
| ATT | TTA | GGC | CAG | ATG | ACG | CTT | CTA | GAG | GGC | AGC | ATT | GCA | ATC AGT GGA | 1918 |
| Ile | Leu | Gly | Gln | Met | Thr | Leu | Leu | Glu | Gly | Ser | Ile | Ala | Ile Ser Gly |
|     | 625 |     |     |     | 630 |     |     |     | 635 |     |     |     |      |

```
                     610                      615                      620
ATT TTA GGC CAG ATG ACG CTT CTA GAG GGC AGC ATT GCA ATC AGT GGA         1918
Ile Leu Gly Gln Met Thr Leu Leu Glu Gly Ser Ile Ala Ile Ser Gly
    625                 630                 635

ACC TTC GCT TAT GTG GCC CAG CAG GCC TGG ATC CTC AAT GCT ACT CTG         1966
Thr Phe Ala Tyr Val Ala Gln Gln Ala Trp Ile Leu Asn Ala Thr Leu
640                 645                 650                 655

AGA GAC AAC ATC CTG TTT GGG AAG GAA TAT GAT GAA GAA AGA TAC AAC         2014
Arg Asp Asn Ile Leu Phe Gly Lys Glu Tyr Asp Glu Glu Arg Tyr Asn
                660                 665                 670

TCT GTG CTG AAC AGC TGC TGC CTG AGG CCT GAC CTG GCC ATT CTT CCC         2062
Ser Val Leu Asn Ser Cys Cys Leu Arg Pro Asp Leu Ala Ile Leu Pro
            675                 680                 685

AGC AGC GAC CTG ACG GAG ATT GGA GAG CGA GGA GCC AAC CTG AGC GGT         2110
Ser Ser Asp Leu Thr Glu Ile Gly Glu Arg Gly Ala Asn Leu Ser Gly
        690                 695                 700

GGG CAG CGC CAG AGG ATC AGC CTT GCC CGG GCC TTG TAT AGT GAC AGG         2158
Gly Gln Arg Gln Arg Ile Ser Leu Ala Arg Ala Leu Tyr Ser Asp Arg
    705                 710                 715

AGC ATC TAC ATC CTG GAC GAC CCC CTC AGT GCC TTA GAT GCC CAT GTG         2206
Ser Ile Tyr Ile Leu Asp Asp Pro Leu Ser Ala Leu Asp Ala His Val
720                 725                 730                 735

GGC AAC CAC ATC TTC AAT AGT GCT ATC CGG AAA CAT CTC AAG TCC AAG         2254
Gly Asn His Ile Phe Asn Ser Ala Ile Arg Lys His Leu Lys Ser Lys
                740                 745                 750

ACA GTT CTG TTT GTT ACC CAC CAG TTA CAG TAC CTG GTT GAC TGT GAT         2302
Thr Val Leu Phe Val Thr His Gln Leu Gln Tyr Leu Val Asp Cys Asp
            755                 760                 765

GAA GTG ATC TTC ATG AAA GAG GGC TGT ATT ACG GAA AGA GGC ACC CAT         2350
Glu Val Ile Phe Met Lys Glu Gly Cys Ile Thr Glu Arg Gly Thr His
        770                 775                 780

GAG GAA CTG ATG AAT TTA AAT GGT GAC TAT GCT ACC ATT TTT AAT AAC         2398
Glu Glu Leu Met Asn Leu Asn Gly Asp Tyr Ala Thr Ile Phe Asn Asn
    785                 790                 795

CTG TTG CTG GGA GAG ACA CCG CCA GTT GAG ATC AAT TCA AAA AAG GAA         2446
Leu Leu Leu Gly Glu Thr Pro Pro Val Glu Ile Asn Ser Lys Lys Glu
800                 805                 810                 815

ACC AGT GGT TCA CAG AAG AAG TCA CAA GAC AAG GGT CCT AAA ACA GGA         2494
Thr Ser Gly Ser Gln Lys Lys Ser Gln Asp Lys Gly Pro Lys Thr Gly
                820                 825                 830

TCA ATA AAG AAG GAA AAA GCA GTA AAG CCA GAG GAA GGG CAG CTT GTG         2542
Ser Ile Lys Lys Glu Lys Ala Val Lys Pro Glu Glu Gly Gln Leu Val
            835                 840                 845

CAG CTG GAA GAG AAA GGG CAG GGT TCA GTG CCC TGG TCA GTA TAT GGT         2590
Gln Leu Glu Glu Lys Gly Gln Gly Ser Val Pro Trp Ser Val Tyr Gly
        850                 855                 860

GTC TAC ATC CAG GCT GCT GGG GGC CCC TTG GCA TTC CTG GTT ATT ATG         2638
Val Tyr Ile Gln Ala Ala Gly Gly Pro Leu Ala Phe Leu Val Ile Met
    865                 870                 875

GCC CTT TTC ATG CTG AAT GTA GGC AGC ACC GCC TTC AGC ACC TGG TGG         2686
Ala Leu Phe Met Leu Asn Val Gly Ser Thr Ala Phe Ser Thr Trp Trp
880                 885                 890                 895

TTG AGT TAC TGG ATC AAG CAA GGA AGC GGG AAC ACC ACT GTG ACT CGA         2734
Leu Ser Tyr Trp Ile Lys Gln Gly Ser Gly Asn Thr Thr Val Thr Arg
                900                 905                 910

GGG AAC GAG ACC TCG GTG AGT GAC AGC ATG AAG GAC AAT CCT CAT ATG         2782
Gly Asn Glu Thr Ser Val Ser Asp Ser Met Lys Asp Asn Pro His Met
            915                 920                 925

CAG TAC TAT GCC AGC ATC TAC GCC CTC TCC ATG GCA GTC ATG CTG ATC         2830
Gln Tyr Tyr Ala Ser Ile Tyr Ala Leu Ser Met Ala Val Met Leu Ile
```

-continued

```
                 930                     935                     940
CTG AAA GCC ATT CGA GGA GTT GTC TTT GTC AAG GGC ACG CTG CGA GCT        2878
Leu Lys Ala Ile Arg Gly Val Val Phe Val Lys Gly Thr Leu Arg Ala
945                     950                     955

TCC TCC CGG CTG CAT GAC GAG CTT TTC CGA AGG ATC CTT CGA AGC CCT        2926
Ser Ser Arg Leu His Asp Glu Leu Phe Arg Arg Ile Leu Arg Ser Pro
960                     965                     970                 975

ATG AAG TTT TTT GAC ACG ACC CCC ACA GGG AGG ATT CTC AAC AGG TTT        2974
Met Lys Phe Phe Asp Thr Thr Pro Thr Gly Arg Ile Leu Asn Arg Phe
                980                     985                     990

TCC AAA GAC ATG GAT GAA GTT GAC GTG CGG CTG CCG TTC CAG GCC GAG        3022
Ser Lys Asp Met Asp Glu Val Asp Val Arg Leu Pro Phe Gln Ala Glu
            995                     1000                    1005

ATG TTC ATC CAG AAC GTT ATC CTG GTG TTC TTC TGT GTG GGA ATG ATC        3070
Met Phe Ile Gln Asn Val Ile Leu Val Phe Phe Cys Val Gly Met Ile
        1010                    1015                    1020

GCA GGA GTC TTC CCG TGG TTC CTT GTG GCA GTG GGG CCC CTT GTC ATC        3118
Ala Gly Val Phe Pro Trp Phe Leu Val Ala Val Gly Pro Leu Val Ile
    1025                    1030                    1035

CTC TTT TCA GTC CTG CAC ATT GTC TCC AGG GTC CTG ATT CGG GAG CTG        3166
Leu Phe Ser Val Leu His Ile Val Ser Arg Val Leu Ile Arg Glu Leu
1040                    1045                    1050                    1055

AAG CGT CTG GAC AAT ATC ACG CAG TCA CCT TTC CTC TCC CAC ATC ACG        3214
Lys Arg Leu Asp Asn Ile Thr Gln Ser Pro Phe Leu Ser His Ile Thr
                1060                    1065                    1070

TCC AGC ATA CAG GGC CTT GCC ACC ATC CAC GCC TAC AAT AAA GGG CAG        3262
Ser Ser Ile Gln Gly Leu Ala Thr Ile His Ala Tyr Asn Lys Gly Gln
            1075                    1080                    1085

GAG TTT CTG CAC AGA TAC CAG GAG CTG CTG GAT GAC AAC CAA GCT CCT        3310
Glu Phe Leu His Arg Tyr Gln Glu Leu Leu Asp Asp Asn Gln Ala Pro
        1090                    1095                    1100

TTT TTT TTG TTT ACG TGT GCG ATG CGG TGG CTG GCT GTG CGG CTG GAC        3358
Phe Phe Leu Phe Thr Cys Ala Met Arg Trp Leu Ala Val Arg Leu Asp
    1105                    1110                    1115

CTC ATC AGC ATC GCC CTC ATC ACC ACC ACG GGG CTG ATG ATC GTT CTT        3406
Leu Ile Ser Ile Ala Leu Ile Thr Thr Thr Gly Leu Met Ile Val Leu
1120                    1125                    1130                    1135

ATG CAC GGG CAG ATT CCC CCA GCC TAT GCG GGT CTC GCC ATC TCT TAT        3454
Met His Gly Gln Ile Pro Pro Ala Tyr Ala Gly Leu Ala Ile Ser Tyr
                1140                    1145                    1150

GCT GTC CAG TTA ACG GGG CTG TTC CAG TTT ACG GTC AGA CTG GCA TCT        3502
Ala Val Gln Leu Thr Gly Leu Phe Gln Phe Thr Val Arg Leu Ala Ser
            1155                    1160                    1165

GAG ACA GAA GCT CGA TTC ACC TCG GTG GAG AGG ATC AAT CAC TAC ATT        3550
Glu Thr Glu Ala Arg Phe Thr Ser Val Glu Arg Ile Asn His Tyr Ile
        1170                    1175                    1180

AAG ACT CTG TCC TTG GAA GCA CCT GCC AGA ATT AAG AAC AAG GCT CCC        3598
Lys Thr Leu Ser Leu Glu Ala Pro Ala Arg Ile Lys Asn Lys Ala Pro
    1185                    1190                    1195

TCC CCT GAC TGG CCC CAG GAG GGA GAG GTG ACC TTT GAG AAC GCA GAG        3646
Ser Pro Asp Trp Pro Gln Glu Gly Glu Val Thr Phe Glu Asn Ala Glu
1200                    1205                    1210                    1215

ATG AGG TAC CGA GAA AAC CTC CCT CTC GTC CTA AAG AAA GTA TCC TTC        3694
Met Arg Tyr Arg Glu Asn Leu Pro Leu Val Leu Lys Lys Val Ser Phe
                1220                    1225                    1230

ACG ATC AAA CCT AAA GAG AAG ATT GGC ATT GTG GGG CGG ACA GGA TCA        3742
Thr Ile Lys Pro Lys Glu Lys Ile Gly Ile Val Gly Arg Thr Gly Ser
            1235                    1240                    1245

GGG AAG TCC TCG CTG GGG ATG GCC CTC TTC CGT CTG GTG GAG TTA TCT        3790
Gly Lys Ser Ser Leu Gly Met Ala Leu Phe Arg Leu Val Glu Leu Ser
```

```
                1250            1255            1260
GGA GGC TGC ATC AAG ATT GAT GGA GTG AGA ATC AGT GAT ATT GGC CTT        3838
Gly Gly Cys Ile Lys Ile Asp Gly Val Arg Ile Ser Asp Ile Gly Leu
        1265            1270            1275

GCC GAC CTC CGA AGC AAA CTC TCT ATC ATT CCT CAA GAG CCG GTG CTG        3886
Ala Asp Leu Arg Ser Lys Leu Ser Ile Ile Pro Gln Glu Pro Val Leu
1280            1285            1290            1295

TTC AGT GGC ACT GTC AGA TCA AAT TTG GAC CCC TTC AAC CAG TAC ACT        3934
Phe Ser Gly Thr Val Arg Ser Asn Leu Asp Pro Phe Asn Gln Tyr Thr
            1300            1305            1310

GAA GAC CAG ATT TGG GAT GCC CTG GAG AGG ACA CAC ATG AAA GAA TGT        3982
Glu Asp Gln Ile Trp Asp Ala Leu Glu Arg Thr His Met Lys Glu Cys
        1315            1320            1325

ATT GCT CAG CTA CCT CTG AAA CTT GAA TCT GAA GTG ATG GAG AAT GGG        4030
Ile Ala Gln Leu Pro Leu Lys Leu Glu Ser Glu Val Met Glu Asn Gly
        1330            1335            1340

GAT AAC TTC TCA GTG GGG GAA CGG CAG CTC TTG TGC ATA GCT AGA GCC        4078
Asp Asn Phe Ser Val Gly Glu Arg Gln Leu Leu Cys Ile Ala Arg Ala
        1345            1350            1355

CTG CTC CGC CAC TGT AAG ATT CTG ATT TTA GAT GAA GCC ACA GCT GCC        4126
Leu Leu Arg His Cys Lys Ile Leu Ile Leu Asp Glu Ala Thr Ala Ala
1360            1365            1370            1375

ATG GAC ACA GAG ACA GAC TTA TTG ATT CAA GAG ACC ATC CGA GAA GCA        4174
Met Asp Thr Glu Thr Asp Leu Leu Ile Gln Glu Thr Ile Arg Glu Ala
            1380            1385            1390

TTT GCA GAC TGT ACC ATG CTG ACC ATT GCC CAT CGC CTG CAC ACG GTT        4222
Phe Ala Asp Cys Thr Met Leu Thr Ile Ala His Arg Leu His Thr Val
        1395            1400            1405

CTA GGC TCC GAT AGG ATT ATG GTG CTG GCC CAG GGA CAG GTG GTG GAG        4270
Leu Gly Ser Asp Arg Ile Met Val Leu Ala Gln Gly Gln Val Val Glu
        1410            1415            1420

TTT GAC ACC CCA TCG GTC CTT CTG TCC AAC GAC AGT TCC CGA TTC TAT        4318
Phe Asp Thr Pro Ser Val Leu Leu Ser Asn Asp Ser Ser Arg Phe Tyr
        1425            1430            1435

GCC ATG TTT GCT GCT GCA GAG AAC AAG GTC GCT GTC AAG GGC                4360
Ala Met Phe Ala Ala Ala Glu Asn Lys Val Ala Val Lys Gly
1440            1445            1450

TGACTCCTCC CTGTTGACGA AGTCTCTTTT CTTTAGAGCA TTGCCMYKGM MTKCCTGGGG       4420

CGGGCCCCTT CATCGCGTCC TCCTACCGAA ACCTTGCCTT TCTCGATTTT ATCTTTCGCA       4480

CAGCAGTTCC GGATTGGCTT GTGTGTTTCA CTTTTAGGGA GAGTCATATT TTGATTATTG       4540

TATTTATTCC ATATTCATGT AAACAAAATT TAGTTTTTGT TCTTAATTGC ACTCTAAAAG       4600

GTTCAGGGAA CCGTTATTAT AATTGTATCA GAGGCCTATA ATGAAGCTTT ATACGTGTAG       4660

CTATATCTAT ATATAATTCT GTACATAGCC TATATTTACA GTGAAAATGT AAGCTGTTTA       4720

TTTTATATTA AAATAAGCAC TGTGCTAAAA AAAAAAAAA AAAAAAAAAA AGGGCGGCCG       4780

C                                                                       4781
```

(2) INFORMATION FOR SEQ ID NO:2:

(i) SEQUENCE CHARACTERISTICS:
        (A) LENGTH: 1453 amino acids
        (B) TYPE: amino acid
        (D) TOPOLOGY: linear (ii) MOLECULE TYPE: protein (xi) SEQUENCE DESCRIPTION: SEQ ID NO:2:

```
Asp Val Lys Leu Thr Val Cys Glu Pro Trp Asn Leu His Ser Glu Lys
1               5                   10                  15
```

```
Met Lys Asp Ile Asp Ile Gly Lys Glu Tyr Ile Ile Pro Ser Pro Gly
                20                  25                  30

Tyr Arg Ser Val Arg Glu Arg Thr Ser Thr Gly Thr His Arg Asp
         35                  40                  45

Arg Glu Asp Ser Lys Phe Arg Arg Thr Arg Pro Leu Glu Cys Gln Asp
         50                  55                  60

Ala Leu Glu Thr Ala Ala Arg Ala Glu Gly Leu Ser Leu Asp Ala Ser
 65                  70                  75                  80

Met His Ser Gln Leu Arg Ile Leu Asp Glu Glu His Pro Lys Gly Lys
                 85                  90                  95

Tyr His His Gly Leu Ser Ala Leu Lys Pro Ile Arg Thr Thr Ser Lys
                100                 105                 110

His Gln His Pro Val Asp Asn Ala Gly Leu Phe Ser Cys Met Thr Phe
             115                 120                 125

Ser Trp Leu Ser Ser Leu Ala Arg Val Ala His Lys Lys Gly Glu Leu
130                 135                 140

Ser Met Glu Asp Val Trp Ser Leu Ser Lys His Glu Ser Ser Asp Val
145                 150                 155                 160

Asn Cys Arg Arg Leu Glu Arg Leu Trp Gln Glu Leu Asn Glu Val
                165                 170                 175

Gly Pro Asp Ala Ala Ser Leu Arg Arg Val Val Trp Ile Phe Cys Arg
                180                 185                 190

Thr Arg Leu Ile Leu Ser Ile Val Cys Leu Met Ile Thr Gln Leu Ala
             195                 200                 205

Gly Phe Ser Gly Pro Ala Phe Met Val Lys His Leu Leu Glu Tyr Thr
             210                 215                 220

Gln Ala Thr Glu Ser Asn Leu Gln Tyr Ser Leu Leu Val Leu Gly
225                 230                 235                 240

Leu Leu Leu Thr Glu Ile Val Arg Ser Trp Ser Leu Ala Leu Thr Trp
                245                 250                 255

Ala Leu Asn Tyr Arg Thr Gly Val Arg Leu Arg Gly Ala Ile Leu Thr
                260                 265                 270

Met Ala Phe Lys Lys Ile Leu Lys Leu Lys Asn Ile Lys Glu Lys Ser
             275                 280                 285

Leu Gly Glu Leu Ile Asn Ile Cys Ser Asn Asp Gly Gln Arg Met Phe
             290                 295                 300

Glu Ala Ala Val Gly Ser Leu Leu Ala Gly Gly Pro Val Val Ala
305                 310                 315                 320

Ile Leu Gly Met Ile Tyr Asn Val Ile Ile Leu Gly Pro Thr Gly Phe
                325                 330                 335

Leu Gly Ser Ala Val Phe Ile Leu Phe Tyr Pro Ala Met Met Phe Ala
                340                 345                 350

Ser Arg Leu Thr Ala Tyr Phe Arg Arg Lys Cys Val Ala Ala Thr Asp
             355                 360                 365

Glu Arg Val Gln Lys Met Asn Glu Val Leu Thr Tyr Ile Lys Phe Ile
370                 375                 380

Lys Met Tyr Ala Trp Val Lys Ala Phe Ser Gln Ser Val Gln Lys Ile
385                 390                 395                 400

Arg Glu Glu Glu Arg Ile Leu Glu Lys Ala Gly Tyr Phe Gln Ser
                405                 410                 415

Ile Thr Val Gly Val Ala Pro Ile Val Val Ile Ala Ser Val Val
             420                 425                 430

Thr Phe Ser Val His Met Thr Leu Gly Phe Asp Leu Thr Ala Ala Gln
```

-continued

```
                435                 440                 445
Ala Phe Thr Val Val Thr Val Phe Asn Ser Met Thr Phe Ala Leu Lys
    450                 455                 460
Val Thr Pro Phe Ser Val Lys Ser Leu Ser Glu Ala Ser Val Ala Val
465                 470                 475                 480
Asp Arg Phe Lys Ser Leu Phe Leu Met Glu Glu Val His Met Ile Lys
                485                 490                 495
Asn Lys Pro Ala Ser Pro His Ile Lys Ile Glu Met Lys Asn Ala Thr
            500                 505                 510
Leu Ala Trp Asp Ser Ser His Ser Ser Ile Gln Asn Ser Pro Lys Leu
        515                 520                 525
Thr Pro Lys Met Lys Lys Asp Lys Arg Ala Ser Arg Gly Lys Lys Glu
    530                 535                 540
Lys Val Arg Gln Leu Gln Arg Thr Glu His Gln Ala Val Leu Ala Glu
545                 550                 555                 560
Gln Lys Gly His Leu Leu Leu Asp Ser Asp Glu Arg Pro Ser Pro Glu
                565                 570                 575
Glu Glu Glu Gly Lys His Ile His Leu Gly His Leu Arg Leu Gln Arg
            580                 585                 590
Thr Leu His Ser Ile Asp Leu Glu Ile Gln Glu Gly Lys Leu Val Gly
        595                 600                 605
Ile Cys Gly Ser Val Gly Ser Gly Lys Thr Ser Leu Ile Ser Ala Ile
    610                 615                 620
Leu Gly Gln Met Thr Leu Leu Glu Gly Ser Ile Ala Ile Ser Gly Thr
625                 630                 635                 640
Phe Ala Tyr Val Ala Gln Gln Ala Trp Ile Leu Asn Ala Thr Leu Arg
                645                 650                 655
Asp Asn Ile Leu Phe Gly Lys Glu Tyr Asp Glu Glu Arg Tyr Asn Ser
            660                 665                 670
Val Leu Asn Ser Cys Cys Leu Arg Pro Asp Leu Ala Ile Leu Pro Ser
        675                 680                 685
Ser Asp Leu Thr Glu Ile Gly Glu Arg Gly Ala Asn Leu Ser Gly Gly
    690                 695                 700
Gln Arg Gln Arg Ile Ser Leu Ala Arg Ala Leu Tyr Ser Asp Arg Ser
705                 710                 715                 720
Ile Tyr Ile Leu Asp Asp Pro Leu Ser Ala Leu Asp Ala His Val Gly
                725                 730                 735
Asn His Ile Phe Asn Ser Ala Ile Arg Lys His Leu Lys Ser Lys Thr
            740                 745                 750
Val Leu Phe Val Thr His Gln Leu Gln Tyr Leu Val Asp Cys Asp Glu
        755                 760                 765
Val Ile Phe Met Lys Glu Gly Cys Ile Thr Glu Arg Gly Thr His Glu
    770                 775                 780
Glu Leu Met Asn Leu Asn Gly Asp Tyr Ala Thr Ile Phe Asn Asn Leu
785                 790                 795                 800
Leu Leu Gly Glu Thr Pro Pro Val Glu Ile Asn Ser Lys Lys Glu Thr
                805                 810                 815
Ser Gly Ser Gln Lys Lys Ser Gln Asp Lys Gly Pro Lys Thr Gly Ser
            820                 825                 830
Ile Lys Lys Glu Lys Ala Val Lys Pro Glu Glu Gly Gln Leu Val Gln
        835                 840                 845
Leu Glu Glu Lys Gly Gln Gly Ser Val Pro Trp Ser Val Tyr Gly Val
    850                 855                 860
```

```
Tyr Ile Gln Ala Ala Gly Gly Pro Leu Ala Phe Leu Val Ile Met Ala
865                 870                 875                 880

Leu Phe Met Leu Asn Val Gly Ser Thr Ala Phe Ser Thr Trp Trp Leu
            885                 890                 895

Ser Tyr Trp Ile Lys Gln Gly Ser Gly Asn Thr Thr Val Thr Arg Gly
        900                 905                 910

Asn Glu Thr Ser Val Ser Asp Ser Met Lys Asp Asn Pro His Met Gln
    915                 920                 925

Tyr Tyr Ala Ser Ile Tyr Ala Leu Ser Met Ala Val Met Leu Ile Leu
930                 935                 940

Lys Ala Ile Arg Gly Val Val Phe Val Lys Gly Thr Leu Arg Ala Ser
945                 950                 955                 960

Ser Arg Leu His Asp Glu Leu Phe Arg Arg Ile Leu Arg Ser Pro Met
            965                 970                 975

Lys Phe Phe Asp Thr Thr Pro Thr Gly Arg Ile Leu Asn Arg Phe Ser
        980                 985                 990

Lys Asp Met Asp Glu Val Asp Val Arg Leu Pro Phe Gln Ala Glu Met
    995                 1000                1005

Phe Ile Gln Asn Val Ile Leu Val Phe Phe Cys Val Gly Met Ile Ala
    1010                1015                1020

Gly Val Phe Pro Trp Phe Leu Val Ala Val Gly Pro Leu Val Ile Leu
1025                1030                1035                1040

Phe Ser Val Leu His Ile Val Ser Arg Val Leu Ile Arg Glu Leu Lys
            1045                1050                1055

Arg Leu Asp Asn Ile Thr Gln Ser Pro Phe Leu Ser His Ile Thr Ser
        1060                1065                1070

Ser Ile Gln Gly Leu Ala Thr Ile His Ala Tyr Asn Lys Gly Gln Glu
    1075                1080                1085

Phe Leu His Arg Tyr Gln Glu Leu Leu Asp Asp Asn Gln Ala Pro Phe
    1090                1095                1100

Phe Leu Phe Thr Cys Ala Met Arg Trp Leu Ala Val Arg Leu Asp Leu
1105                1110                1115                1120

Ile Ser Ile Ala Leu Ile Thr Thr Thr Gly Leu Met Ile Val Leu Met
            1125                1130                1135

His Gly Gln Ile Pro Pro Ala Tyr Ala Gly Leu Ala Ile Ser Tyr Ala
        1140                1145                1150

Val Gln Leu Thr Gly Leu Phe Gln Phe Thr Val Arg Leu Ala Ser Glu
    1155                1160                1165

Thr Glu Ala Arg Phe Thr Ser Val Glu Arg Ile Asn His Tyr Ile Lys
    1170                1175                1180

Thr Leu Ser Leu Glu Ala Pro Ala Arg Ile Lys Asn Lys Ala Pro Ser
1185                1190                1195                1200

Pro Asp Trp Pro Gln Glu Gly Glu Val Thr Phe Glu Asn Ala Glu Met
            1205                1210                1215

Arg Tyr Arg Glu Asn Leu Pro Leu Val Leu Lys Lys Val Ser Phe Thr
        1220                1225                1230

Ile Lys Pro Lys Glu Lys Ile Gly Ile Val Gly Arg Thr Gly Ser Gly
    1235                1240                1245

Lys Ser Ser Leu Gly Met Ala Leu Phe Arg Leu Val Glu Leu Ser Gly
    1250                1255                1260

Gly Cys Ile Lys Ile Asp Gly Val Arg Ile Ser Asp Ile Gly Leu Ala
1265                1270                1275                1280

Asp Leu Arg Ser Lys Leu Ser Ile Ile Pro Gln Glu Pro Val Leu Phe
            1285                1290                1295
```

```
Ser Gly Thr Val Arg Ser Asn Leu Asp Pro Phe Asn Gln Tyr Thr Glu
        1300                1305                1310

Asp Gln Ile Trp Asp Ala Leu Glu Arg Thr His Met Lys Glu Cys Ile
        1315                1320                1325

Ala Gln Leu Pro Leu Lys Leu Glu Ser Glu Val Met Glu Asn Gly Asp
        1330                1335                1340

Asn Phe Ser Val Gly Glu Arg Gln Leu Leu Cys Ile Ala Arg Ala Leu
1345                1350                1355                1360

Leu Arg His Cys Lys Ile Leu Ile Leu Asp Glu Ala Thr Ala Ala Met
                1365                1370                1375

Asp Thr Glu Thr Asp Leu Leu Ile Gln Glu Thr Ile Arg Glu Ala Phe
        1380                1385                1390

Ala Asp Cys Thr Met Leu Thr Ile Ala His Arg Leu His Thr Val Leu
        1395                1400                1405

Gly Ser Asp Arg Ile Met Val Leu Ala Gln Gly Gln Val Val Glu Phe
        1410                1415                1420

Asp Thr Pro Ser Val Leu Leu Ser Asn Asp Ser Ser Arg Phe Tyr Ala
1425                1430                1435                1440

Met Phe Ala Ala Ala Glu Asn Lys Val Ala Val Lys Gly
                1445                1450
```

(2) INFORMATION FOR SEQ ID NO:3:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO:3:

```
GCGTCCGCCT AGAACGCAGA GATGAGGTAC CGAGAAAACC TCCCTCTCGT CCTAAAGAAA      60

GTATCCTTCA CGATCAAACC TAAAGAGAAG ATTGGCATTG TGGGGCGGAC AGGATCAGGG     120

AAGTCCTCGC TGGGGATGGC CCTCTTCCGT CTGGTGGAGT TATCTGGAGG CTGCATCAAG     180

ATTGATGGAG TGAGAATCAG TGATATTGGC CTTGCCGACC TCCGAAGCAA ACTCTCTATC     240

ATTCCTCAAG AGCCGGTGCT GTTCAGTGGC ACTGTCAGAT CAAATTTGGA CCCCTTCAACC    300

AGTACACTGA AGACCAGATT TGGGATGCCC TGGAAAGGAC ACACATGAAA GAATGTATTG     360

CTCCAGCTAC CTCCTGAAAC TTGAATCCTG AATTTGATGG AGAAATGGGG AAATAACTTC     420

TCCAGTTGGG GGAAACGGCA CTCTTTGTTG CCATACCTAN ACC                       463
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

```
TGCTGGTTCT CTCCCTCACA CTTC                                             24
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
        (xi) SEQUENCE DESCRIPTION: SEQ ID NO:5:

CTCGGCTCGG GCTGCTGTTT CCAA                                              24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

GGGTGCTGGT GTTTGGAAGT AGTC                                              24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

GCCAGAGAAG AAAGCCACGA AAAA                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

AGGCACACGA TGGACAGGAT GAGC                                              24
```

What is claimed is:

1. An isolated nucleic acid molecule which encodes an MRP-β polypeptide which functions to transport, expel, or sequester substances from an intracellular milieu, wherein the nucleic acid molecule hybridizes to a nucleic acid molecule having the nucleotide sequence of SEQ ID NO: 1, or a complement thereof, under conditions of hybridization in 0.5M NaHPO$_4$ at 65° C. followed by washing in 0.1× SSC at 68° C.

2. The isolated nucleic acid molecule of claim 1 comprising the nucleotide sequence of SEQ ID NO: 1 or the complement thereof.

3. The isolated nucleic acid molecule of claim 1 comprising the nucleotide sequence of SEQ ID NO: 1.

4. The isolated nucleic acid molecule of claim 1 consisting of the nucleotide sequence of SEQ ID NO: 1.

5. An expression vector comprising the nucleic acid molecule of any of claims 1 to 4.

6. A cell transfected with the expression vector of claim 5.

7. A cell of claim 6 that is immortalized under cell culture conditions.

8. A cell of claim 6 that is of human origin.

9. A cell of claim 6 that is a unicellular organism.

10. A cell of claim 6 that is a yeast cell.

* * * * *